United States Patent
Elser

(10) Patent No.: US 8,398,560 B2
(45) Date of Patent: Mar. 19, 2013

(54) EQUINE WIRELESS PHYSIOLOGICAL MONITORING SYSTEM

(75) Inventor: Andrew H. Elser, West Chester, PA (US)

(73) Assignee: Andrew H. Elser, PC, Lewisville, PA (US)

( * ) Notice: Subject to any disclaimer, the term of this patent is extended or adjusted under 35 U.S.C. 154(b) by 435 days.

(21) Appl. No.: 11/273,678

(22) Filed: Nov. 14, 2005

(65) Prior Publication Data

US 2006/0106289 A1    May 18, 2006

Related U.S. Application Data

(60) Provisional application No. 60/627,215, filed on Nov. 12, 2004.

(51) Int. Cl.
*A61B 5/08* (2006.01)
*A61B 5/103* (2006.01)

(52) U.S. Cl. ........................ 600/534; 600/595

(58) Field of Classification Search .......... 600/529–543, 600/544–547, 300, 301, 481, 483, 484, 508, 600/509, 549, 595
See application file for complete search history.

(56) References Cited

U.S. PATENT DOCUMENTS

| | | | |
|---|---|---|---|
| 1,057,529 A | 4/1913 | Cloninger | |
| 3,695,253 A | 10/1972 | Vielhauer | |
| 3,990,435 A | 11/1976 | Murphy | |
| 4,218,584 A | 8/1980 | Attenburrow | |
| 4,258,718 A * | 3/1981 | Goldman | 600/409 |
| 4,261,293 A | 4/1981 | Djernes | |
| 4,360,030 A * | 11/1982 | Citron et al. | 600/515 |
| 4,364,397 A * | 12/1982 | Citron et al. | 600/523 |
| 4,417,306 A * | 11/1983 | Citron et al. | 600/521 |
| 4,720,866 A | 1/1988 | Elias et al. | |
| 4,774,679 A | 9/1988 | Carlin | |
| 4,935,887 A | 6/1990 | Abdalah et al. | |
| 4,955,372 A | 9/1990 | Blackmer et al. | |
| 5,058,600 A | 10/1991 | Schechter et al. | |
| 5,097,706 A | 3/1992 | Le Nouvel et al. | |
| 5,138,550 A | 8/1992 | Abraham et al. | |
| 5,165,417 A | 11/1992 | Murphy, Jr. | |
| 5,263,491 A * | 11/1993 | Thornton | 600/587 |
| 5,309,922 A | 5/1994 | Schechter et al. | |
| 5,461,193 A | 10/1995 | Schertler | |
| 5,503,141 A | 4/1996 | Kettl et al. | |
| 5,566,645 A | 10/1996 | Cole | |
| 5,737,280 A | 4/1998 | Kokubo | |

(Continued)

FOREIGN PATENT DOCUMENTS

| | | |
|---|---|---|
| DE | 198 34 257 C2 | 2/2000 |
| DE | 199 11 766 A1 | 9/2000 |

(Continued)

OTHER PUBLICATIONS

Barrey, E. et al., "Lameness detection using an accelerometric device," Pferdeheilkunde 12, pp. 617-622, (1996).

(Continued)

*Primary Examiner* — Navin Natnithithadha

(74) *Attorney, Agent, or Firm* — Panitch Schwarze Belisario & Nadel LLP

(57) ABSTRACT

An accelerometer senses equine respiratory structural vibrations. The accelerometer includes a sensing surface configured to be attached to one of hair, skin, bone, ligament, cartilage, and other tissue of a horse. The accelerometer is responsive to respiratory structural vibrations of the horse and outputs a signal corresponding to the respiratory structural vibrations.

3 Claims, 21 Drawing Sheets

U.S. PATENT DOCUMENTS

| | | | |
|---|---|---|---|
| 5,737,429 A | 4/1998 | Lee | |
| 5,782,240 A | 7/1998 | Raviv et al. | |
| 5,853,005 A | 12/1998 | Scanlon | |
| 5,889,871 A | 3/1999 | Downs, Jr. | |
| 5,955,667 A | 9/1999 | Fyfe | |
| 6,168,568 B1 | 1/2001 | Gavriely | |
| 6,228,037 B1 | 5/2001 | Derksen | |
| 6,287,264 B1 | 9/2001 | Hoffman | |
| 6,366,855 B1 | 4/2002 | Reilly et al. | |
| 6,443,907 B1 * | 9/2002 | Mansy et al. | 600/529 |
| 6,504,483 B1 | 1/2003 | Richards et al. | |
| 6,513,532 B2 | 2/2003 | Mault et al. | |
| 6,517,497 B2 | 2/2003 | Rymut et al. | |
| 6,551,252 B2 * | 4/2003 | Sackner et al. | 600/536 |
| 6,602,209 B2 | 8/2003 | Lambert et al. | |
| 6,659,960 B2 | 12/2003 | Derksen et al. | |
| 6,723,055 B2 * | 4/2004 | Hoffman | 600/538 |
| 6,736,759 B1 | 5/2004 | Stubbs et al. | |
| 6,771,999 B2 * | 8/2004 | Salla et al. | 600/413 |
| 6,952,912 B2 | 10/2005 | Lambert | |
| 6,997,882 B1 * | 2/2006 | Parker et al. | 600/534 |
| 7,028,547 B2 | 4/2006 | Shiratori | |
| 7,062,895 B1 | 6/2006 | Sperie | |
| 7,094,206 B2 * | 8/2006 | Hoffman | 600/529 |
| 7,467,603 B2 * | 12/2008 | Davies | 119/712 |
| 7,627,451 B2 * | 12/2009 | Vock et al. | 702/178 |
| 7,844,317 B2 * | 11/2010 | Salla et al. | 600/407 |
| 2002/0010390 A1 | 1/2002 | Guice et al. | |
| 2002/0103610 A1 | 8/2002 | Bachmann et al. | |
| 2002/0156391 A1 | 10/2002 | Derksen et al. | |
| 2003/0018276 A1 * | 1/2003 | Mansy et al. | 600/529 |
| 2003/0151554 A1 | 8/2003 | McCarthy | |
| 2004/0183283 A1 | 9/2004 | Buckman et al. | |
| 2004/0225203 A1 | 11/2004 | Jemison et al. | |
| 2004/0243005 A1 | 12/2004 | Rapps | |
| 2005/0277842 A1 * | 12/2005 | Silva | 600/534 |
| 2006/0000420 A1 | 1/2006 | Martin Davies | |

FOREIGN PATENT DOCUMENTS

| | | |
|---|---|---|
| DE | 19911766 | 9/2000 |
| FR | 2839362 | 11/2003 |
| GB | 2347503 A | 6/2000 |
| NZ | 329288 | 8/2001 |
| SE | 003763 | 11/1994 |
| WO | WO 2004/084624 A1 | 10/2004 |
| WO | 2008004111 A2 | 10/2008 |

OTHER PUBLICATIONS

Souzou, S. et al., Abstract and third-party evaluation of Japanese Patent Application No. 2001JP-212911, "Body state monitoring apparatus in hospital, evaluates biological information regarding body state, based on detection output of acceleration, angular velocity and pulse wave sensors," date unknown.

Souzou, S. et al., Abstract of Japanese Patent Publication No. 2003-024287, "Monitor Device for Body State," (2003).

Kusunose, R., et al., "Reliability of EquiPilot® for Measuring Aerobic Fitness in Racehorses," J. Equine Sci. vol. 13, No. 4, pp. 117-121, (2002).

Keegan, K.G., et al., "Accelerometer-Based System for the Detection of Lameness in Horses," Biomed Sci Instrum, 38:102-12, (2002).

Leleu, C., et al., "Reproducibility of a locomotor test for trotter horses," The Veterinary Journal, 168, pp. 160-166, (2004).

Keegan, K.G., et al., "Evaluation of a sensor-based system of motion analysis for detection and quantification of forelimb and hind limb lameness in horses," AJVR, vol. 65, No. 5, (May 2004).

Attenburrow, D. P., "Quantitative and Qualitative Analysis of Respiratory Sounds Recorded from Normal and Abnormal Horses during Vigorous Exercise in the Field," The Veterinary Annual, vol. 36, pp. 280-300, (1996).

Attenburrow, D. P., et al., "The mechanical coupling of lung ventilation to locomotion in the horse," Med. Eng. Phys., vol. 16, pp. 188-192, (May 1994).

Franklin, S. H., et al., "Spectral analysis of respiratory noise in horses with upper airway disorders," Equine Veterinary Journal, 35(d) pp. 264-268, (2003).

Franklin, S. H., et al., "Spectral Analysis of Respiratory Noise in Horses with Upper Airway Obstructions," Veterinary Comparative Respiratory Society Abstract, (2001).

Cable, C., et al., "Sound signature for identification and quantification of upper airway disease in horses," AJVR, vol. 63, No. 12, pp. 1707-1713, (Dec. 2002).

Cable, C. S., et al., "Spectrotemporal Signature for Identifying Upper Airway Abnormalities in Exercising Horses," Veterinary Comparative Respiratory Society, Abstract, (2001).

Brown, J. A., et al., "Ventriculocordectomy reduces respiratory noise in horses with laryngeal hemiplegia," Equine Vetrinary Journal, 35(6) pp. 570-574, (2003).

Derksen, F. J., et al., "Spectrum analysis of respiratory sounds in exercising horses with experimentally induced laryngeal hemiplegia or dorsal displacement of the soft palate," AJVR, vol. 62, No. 5, pp. 659-664, (May 2001).

Galloux, P., et al., "Analysis of equine gait using three-dimensional accelerometers fixed on the saddle," Animal Locomotion, Equine vet. J. Suppl. 17 pp. 44-47, (1994).

Barrey, E., "Methods, Applications and Limitations of Gait Analysis in Horses," The Veterinary Journal, 157, pp. 7-22, (1999).

Barrey, E., et al., "Utilisation of an accelerometric device in equine gait analysis," Animal Locomotion, Equine vet. J. Suppl. 17 pp. 7-12, (1994).

Leleu, C. et al., "Effect of age on locomotion of Standardbred trotters in training," Equinine and Comparative Exercise Physiology 1(2); pp. 107-117 (2004).

Ainsworth, D. M., et al., "Pulmonary-locomotory interactions in exercising dogs and horses," Respiration Physiology 110, pp. 287-294, (1997).

Ainsworth, D., et al., "The effect of exercise on diaphragmatic activation in horses," Respiration Physiology 106, pp. 35-46, (1996).

Young, I. S., "The synchronization of ventilation and locomotion in horses (Equus caballus)," J. exp. Biol. 166, pp. 19-31, (1992).

Lafortuna, C. L., et al., "The effects of locomotor-respiratory coupling on the pattern of breathing in horses," J. of Physiology, 492 (PT2) pp. 587-96, (Apr. 15, 1996).

Butler, P. J., et al., "Stride length and respiratory tidal volume in exercising thoroughbred horses," Respiration Physiology, vol. 98, pp. 51-56, (1993).

Butler, P. J., et al., "Respiratory and Cardiovascular Adjustments During Exercise of Increasing Intensity and During Recovery in Thoroughbred Horses," J. exp. Biol., 179, pp. 159-180 (1993).

Barnes, G.R.G., et al., "Sound spectography in the diagnosis of equine respiratory disorders: a preliminary report," New Zealand Veterinary Journal, vol. 27, pp. 145-146 (1979).

Laca, E. A., et al., "Acoustic measurement of intake and grazing behaviour of cattle," Grass and Forage Science, 55, pp. 97-104, (May 13, 1999).

Belknap, J. K., et al., "Failure of subtotal arytenoidectomy to improve upper airway flow mechanics in exercising Standardbreds with induced laryngeal hemiplegia," Am J Vet Res, vol. 51, No. 9, pp. 1481-1487, (Sep. 1990).

Bramble, D. M., et al., "Running and Breathing in Mammals," Science, vol. 219, pp. 251-256, (Jan. 21, 1983).

Attenburrow, D. P., "Time relationship between the respiratory cycle and limb cycle in the horse," Equine Veterinary Journal, 14(1), pp. 69-72, (1982).

Hornicke, H., et al., "Respiration in Exercising Horses," Equine Exercise Physiology, pp. 7-16, (1987).

Attenburrow, D. P., "Respiration and Locomotion," Equine Exercise Physiology, pp. 17-22, (1984).

Hobo, S., et al., "Characteristics of respiratory function during swimming exercise in thoroughbreds," J. Vet. Med. Sci. 60(6), pp. 687-689 (1998).

Art, T., et al., "Pulmonary Mechanics During Treadmill Exercise in Race Ponies," Veterinary Research Communications, pp. 245-258, (1988).

Subburaj, S., et al., "Methods of Recording and Analysing Cough Sounds," Pulmonary Pharmacology 9, pp. 269-279, (1996).

Lindell, C., "Limited Geographic Variation in the Vocalizations of a Neotropical Furnariid, *Synallaxis Albescens*," Wilson Bull., 110(3), pp. 368-374 (1998).

Perez-Padilla, J. R., et al., "Characteristics of the Snoring Noise in Patients with and without Occlusive Sleep Apnea," Am Rev Respir Dis., vol. 147, pp. 635-644, (1993).

Fletcher, S., et al., "Onboard acoustic recording from diving northern elephant seals," J Acoust Soc Am. 100 (4) Pt. 1, pp. 2531-2539, (Oct. 1996).

Pasterkamp, H., et al., "Measurement of Respiratory Acoustical Signals Comparison of sensors," Chest. 104(5), pp. 1518-1525 (Nov. 1993).

Laca, E. A., et al., "An integrated methodology for studying short-term grazing behaviour of cattle," Grass and Forage Science, vol. 47, pp. 81-90, (1992).

Snidecor, J. C., et al., "Speech Pickup by Contact Microphone at Head and Neck Positions," Journal of Speech and Hearing Research, vol. 2, No. 3, pp. 277-281, (Sep. 1959).

Chambers, A. R. M., et al., "The development and use of equipment for the automatic recording of ingestive behaviour in sheep and cattle," Grass and Forage Science, vol. 36, pp. 97-105, (1981).

Parente, E. J., et al., "Upper Respiratory Dysfunctions in Horses During High-Speed Exercise," American Association of Equine Practitioners, AAEP 40th Annual Convention Proceedings, pp. 81-82 (1994).

Ducharme, N. G., et al., *Current Therapy in Equine Medicine*, "Intermittent Dorsal Displacement of the Soft Palate," W. B. Saunders, Philadelphia, PA, pp. 415-418, (1997).

Seeherman, H. J., *Current Therapy in Equine Medicine*, "Left Recurrent Laryngeal Neuropathy," W. B. Saunders, Philadelphia, PA, pp. 404-407.

Derksen, F. J., et al., "Spectrogram Analysis of Respiratory Sounds in Exercising Horses," Sports Medicine, AAEP Proceedings, pp. 314-315, vol. 45, (1999).

Attenburrow, D. P., "Respiratory Airflow and Sound Intensity," Equine Exercise Physiology, pp. 23-26, (1983).

Attenburrow, D. P., "The Development of a Radio-Stethoscope for use in the Horse at Rest and during Exercise," Equine vet. J., pp. 14-17, 10(1), (1978).

Attenburrow, D. P., "Some Observations on the Sound Vibrations Produced by Air Flow in the Respiratory Tract of Horses at Exercise," Veterinary Annual, 6 pgs., (1971).

Attenburrow, D. P., "Respiratory Sounds recorded by Radio-Stethoscope from Normal Horses at exercise," Equine vet. J., 10(3),pp. 176-179, (1978).

Attenburrow, D. P., "Resonant Frequency of the Lateral Ventrical and Saccule and 'Whistling'," Equine Exercise Physiology, pp. 27-32, (1983).

DolphinEAR Specs., printout from website <http://www.dolphinear.com/de-specs.htm>, 2 pages, printout dated Nov. 11, 2005.

Application Specification sheet for Accelerometer ACH-01, 4 pages, (Dec. 30, 2000 Rev. F).

Art, T., et al., Mechanics of breathing during strenuous exercise in thoroughbred horses, Respiration Physiology, 82:279, (1990).

Hori, Yoshiyuki, et al.; "Distributional Analyses of an Index of Nasal Coupling (HONC) in Simulated Hypernasal Speech;" Cleft Palate Journal; vol. 18, No. 4, pp. 279-285; Oct. 1981.

Horii, Yoshiyuki; "An Accelerometric Approach to Nasality Measurement: A Preliminary Report;" Cleft Palate Journal; vol. 17, No. 3, pp. 254-261; Jul. 1980.

Office Action issued Jul. 26, 2010 in AU Application No. 2005304613.

EP Search Report issued Apr. 21, 2011 in EP Application No. 05820766.3.

Int'l Preliminary Report on Patentability issued Mar. 12, 2009 in Int'l Application No. PCT/US2005/041146.

Office Action issued May 9, 2012 in CA Application No. 2587875.

* cited by examiner

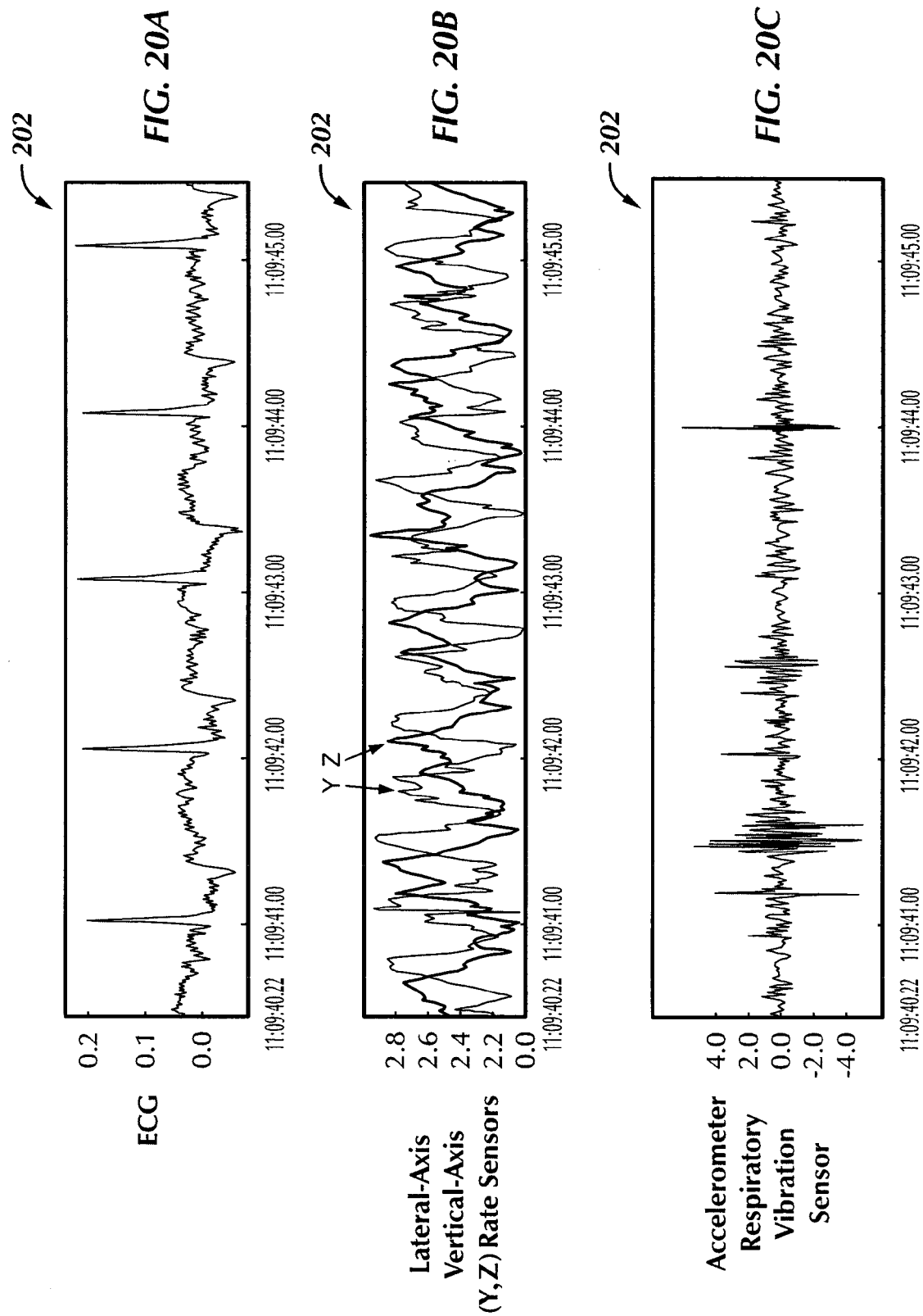

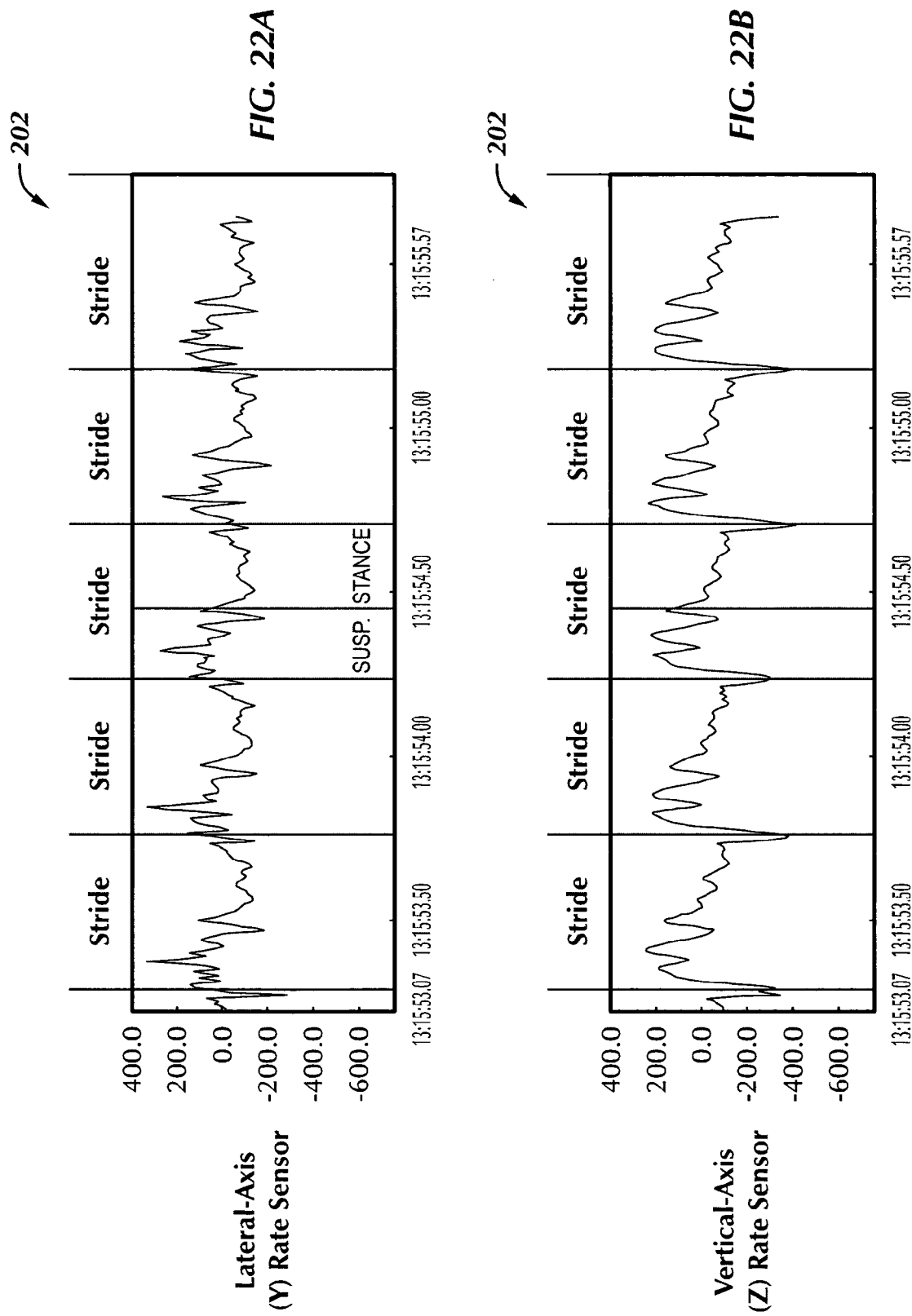

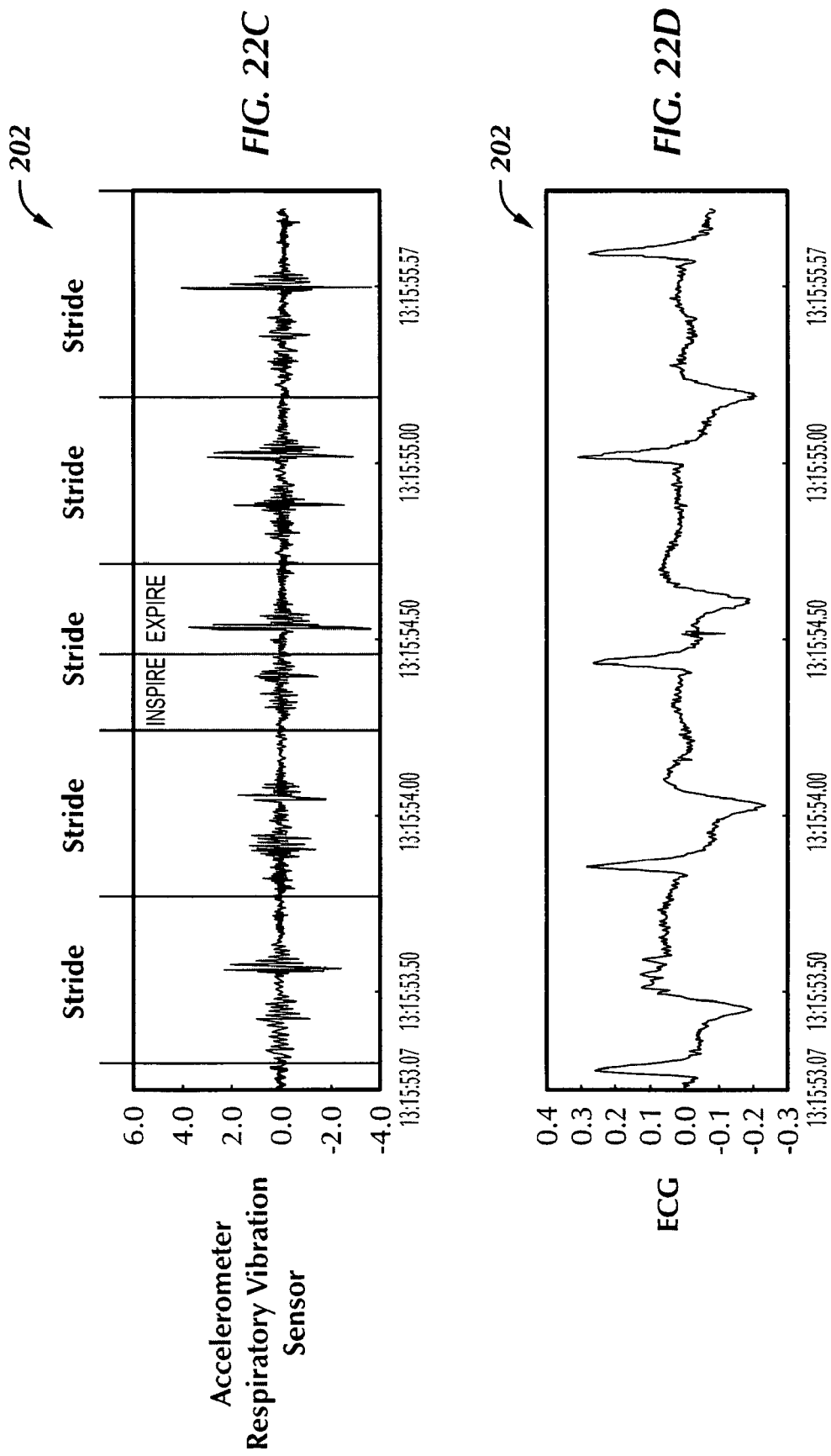

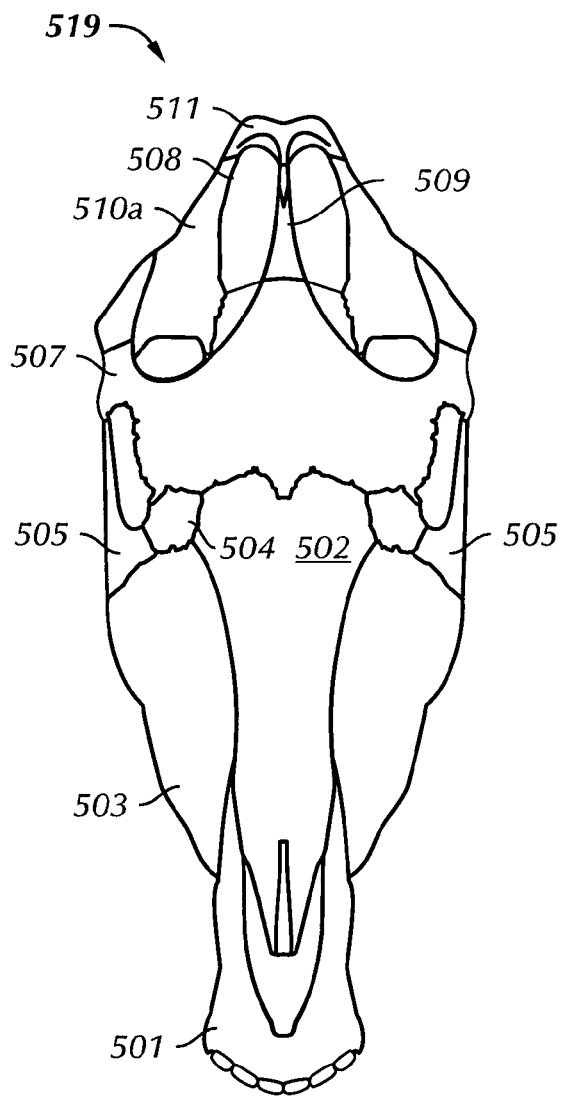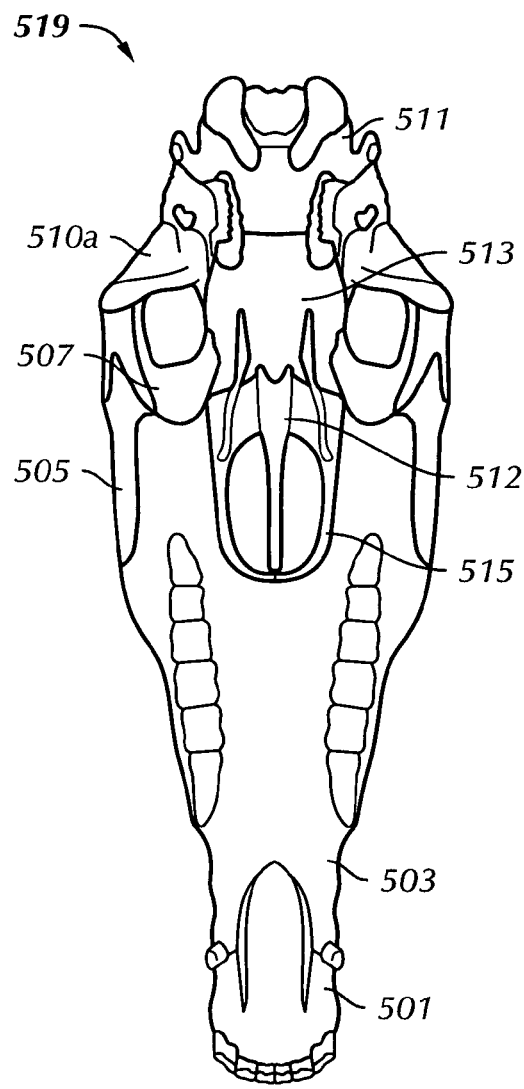
FIG. 25
(PRIOR ART)
FIG. 26
(PRIOR ART)

EQUINE WIRELESS PHYSIOLOGICAL MONITORING SYSTEM

CROSS REFERENCE TO RELATED APPLICATIONS

This application claims priority to U.S. Provisional Patent Application. No. 60/627,215 filed on Nov. 12, 2004, entitled "Equine Wireless Physiological Monitoring System."

BACKGROUND OF THE INVENTION

The present invention relates to an apparatus and procedure to identify the interactions between the respiratory, locomotor, and cardiovascular systems of the exercising horse. The present invention relates to an equine physiological monitoring system, and more particularly, to a portable wireless equine physiological monitoring system and a method for using the equine physiological monitoring system.

Evaluating the interrelationships between the respiratory, locomotor, and cardiovascular systems is valuable in the understanding of equine exercise physiology. In order to study these relationships suitable devices and methods are needed to first detect the individual functions such that the combined functions and relationships can be assessed. It is desirable for these devices and methods to be usable and adaptable to a wide variety of conditions under which the exercising horse may be placed.

It is desirable therefore to design a system of suitable devices, communication and methods of using said system devices and communication simultaneously such that interrelationships of the respiratory, locomotor, and cardiovascular systems of the exercising horse can be accurately studied. To assist in this assessment, it is desirable to provide an accelerometer that senses equine respiratory structural vibrations. It is also desirable to provide an equine motion sensor utilizing angular rate and accelerometer sensors to detect equine locomotion.

Further, it is desirable to provide a wireless system disposed on a horse or proximate to the horse that is configured to monitor equine physiological systems. It is also desired that the system presents the data suitable for the study of the physiological interactions of the exercising horse.

Moreover, it is desirable to provide a wireless equine physiological monitoring system for monitoring interactions of physiological events of an exercising horse. It is desirable to provide a wireless equine physiological monitoring system for monitoring interactions of physiological events of an exercising horse such as electrocardiographic data, respiratory data, motion data, speed or the like. Even further, it is desirable to provide an equine physiological monitoring system for monitoring interactions of physiological events of an exercising horse that collects or stores data which is synchronized with respect to time.

BRIEF SUMMARY OF THE INVENTION

Briefly stated the present invention comprises an accelerometer that senses equine respiratory structural vibrations. The accelerometer includes a sensing surface configured to be attached to one of hair, skin, bone, ligament, cartilage, and other tissue of a horse. The accelerometer is responsive to respiratory structural vibrations of the horse and outputs a signal corresponding to the respiratory structural vibrations.

The present invention also comprises a motion sensor that senses equine motion in multi-dimensional space. The motion sensor includes at least one angular rate sensor and at least one accelerometer. The at least one angular rate sensor and the at least one accelerometer are configured to be mounted proximate to a horse so as to move with the horse. The at least on angular rate sensor detects angular rotation data relative to a first-axis. The at least one accelerometer is mounted proximate to the at least one angular rate sensor and is configured to output multi-dimensional motion data of the horse.

The present invention also comprises a speed sensor that senses equine speed. The speed sensor includes an accelerometer that detects acceleration and deceleration in a longitudinal-axis of a horse and a lateral-axis angular rate sensor configured to be mounted proximate to the accelerometer. The longitudinal-axis is defined through a length of the horse as measured between the cranial and the caudal aspects of the horse. The accelerometer is configured to be mounted proximate to the horse. The lateral-axis angular rate sensor detects angular rotation data relative to the lateral-axis of the horse. The lateral-axis being defined through a width of the body of the horse as measured between the right and left lateral sides of the horse.

The present invention also comprises a speed sensor that senses equine speed. The speed sensor includes a global positioning system (GPS) receiver that receives GPS data from GPS satellites. The GPS receiver updates GPS data at least once per second. The GPS receiver is configured to be mounted proximate to a horse so as to move with the horse. The GPS receiver is configured to perform at least one of outputting data proportional to speed and calculating speed of the horse from the updated GPS data.

The present invention also comprises a speed sensor that senses equine speed. The speed sensor includes at least one Doppler transceiver that transmits an electromagnetic signal and receives a reflected or transponded version of the electromagnetic signal. The at least one Doppler transceiver is configured to be mounted proximate to a horse so as to move with the horse. The at least one Doppler transceiver is configured to perform at least one of outputting data proportional to speed and calculating speed of the horse based on the difference in time/frequency between the transmitted and received electromagnetic signal.

The present invention also comprises a wireless equine physiological monitoring system that includes a respiratory sensor and a memory. The respiratory sensor is configured to be mounted proximate to a horse. The respiratory sensor detects respiratory data of the horse and outputs the detected respiratory data of the horse. The memory at least temporarily stores the detected respiratory data. The detected respiratory data is synchronized with respect to time.

The present invention also comprises a wireless equine physiological monitoring system. The wireless equine physiological monitoring system includes a respiratory detection sensor configured to be mounted proximate to a horse and a memory configured to be mounted proximate to the horse. The respiratory detection sensor detects and outputs detected respiratory data. The memory at least temporarily stores the detected respiratory data of the horse. The detected respiratory data is synchronized with respect to real time. The wireless equine physiological monitoring system also includes a real time trend display that wirelessly receives the detected respiratory data. The trend display displays the detected respiratory data with respect to time as the detected respiratory data is received.

The present invention also comprises a wireless equine physiological monitoring system. The wireless equine physiological monitoring system includes a speed sensor configured to be mounted proximate to a horse. The speed sensor detects and outputs detected speed data of the horse. The wireless equine physiological monitoring system also includes a real-time trend display that wirelessly receives the detected speed data. The trend display displays the detected speed data with respect to time as the detected speed data is received.

The present invention also comprises a wireless equine physiological monitoring system. The wireless equine physiological monitoring system includes a single-axis angular rate sensor configured to be mounted proximate to a horse so as to move with the horse. The single-axis angular rate sensor detects and outputs angular rotation data relative to the single-axis. The single-axis is one of a lateral-axis, a vertical-axis and a longitudinal-axis. The lateral-axis is defined through a width of the body of the horse as measured between the right and left lateral sides of the horse, the vertical-axis is defined through a height of the body of the horse as measured between the dorsal and ventral aspects of the horse and the longitudinal-axis is defined through a length of the horse as measured between the cranial and the caudal aspects of the horse. The wireless equine physiological monitoring system also includes a real-time trend display that wirelessly receives the detected angular rotation data relative to the single-axis. The trend display displays the detected angular rotation data relative to the single-axis with respect to time as the detected angular rotation data relative to the single-axis is received.

The present invention also comprises a wireless equine physiological monitoring system. The wireless equine physiological monitoring system includes a respiratory detection sensor and a second sensor, each configured to be mounted proximate to the horse. The respiratory detection sensor detects and outputs detected respiratory data. The second sensor detects and outputs detected second sensor data. The second sensor is at least one of a lateral-axis angular rate sensor, a longitudinal-axis angular rate sensor, a vertical-axis angular rate sensor, an accelerometer, a speed sensor, an electrocardiogram (ECG) electrode configuration set, an electromyography (EMG) sensor configuration set, an electroencephalograph (EEG) sensor configuration set, electrooculogram (EOG) sensor configuration set, an impedance pneumogram (ZPG) sensor configuration set, a pressure sensor, a gas flow sensor, a gas detection sensor, a pH sensor, a temperature sensor, an imaging sensor, an optical sensor and a blood constituent sensor. The wireless equine physiological monitoring system also includes one of a trend display and a computer that wirelessly receives the detected respiratory data and the detected second sensor data. The respective one of the trend display and the computer displays at least one of the detected respiratory data and the detected second sensor data. The detected respiratory data and the detected second sensor data are synchronized with respect to real time.

The present invention also comprises a wireless equine physiological monitoring system. The wireless equine physiological monitoring system includes a speed sensor and a second sensor, each configured to be mounted proximate to the horse. The speed sensor detects and outputs at least one of detected raw data for calculating speed and calculated speed data. The second sensor detects and outputs detected second sensor data. The second sensor is at least one of a lateral-axis angular rate sensor, a longitudinal-axis angular rate sensor, a vertical-axis angular rate sensor, an accelerometer, a respiratory detection sensor, an ECG electrode configuration set, an EMG sensor configuration set, an EEG sensor configuration set, EOG sensor configuration set, a ZPG sensor configuration set, a pressure sensor, a gas flow sensor, a gas detection sensor, a pH sensor, a temperature sensor, an imaging sensor, an optical sensor and a blood constituent sensor. The wireless equine physiological monitoring system also includes one of a trend display and a computer that wirelessly receives the detected second sensor data and at least one of detected raw data for calculating instantaneous speed and calculated instantaneous speed data. The respective one of the trend display and the computer displays the detected second sensor data and at least one of the detected raw data for calculating instantaneous speed and the calculated instantaneous speed data. The second sensor data and at least one of the detected raw data for calculating instantaneous speed and the calculated instantaneous speed data are synchronized with respect to time.

The present invention also comprises an equine physiological monitoring system. The equine physiological monitoring system includes a portable controller having a memory, a lateral-axis angular rate sensor, a vertical-axis angular rate sensor, an ECG electrode configuration set and a respiratory detection sensor. All of the devices are configured to be mounted proximate to a horse so as to move with the horse. The lateral-axis angular rate sensor is in communication with the controller and sends the controller detected angular rotation data relative to the lateral-axis. The vertical-axis angular rate sensor is in communication with the controller and sends the controller detected angular rotation data relative to the vertical-axis. The ECG electrode configuration set is in communication with the controller and sends the controller detected ECG data. The respiratory detection sensor is in communication with the controller and sends the controller detected respiratory data. The memory at least temporarily stores the detected angular rotation data relative to the lateral-axis, the detected angular rotation data relative to the vertical-axis, the detected ECG data and the detected respiratory data. The detected angular rotation data relative to the lateral-axis, the detected angular rotation data relative to the vertical-axis, the detected ECG data and the detected respiratory data are synchronized with respect to time.

The present invention also comprises a method of monitoring physiological data of an exercising horse. The method includes mounting a sensing surface of an accelerometer directly to one of hair and skin of a horse. The accelerometer detects respiratory structural vibration data. The horse is exercised. The respiratory structural vibration data is stored, at least temporarily, in a memory.

The present invention also comprises a method of monitoring physiological data of an exercising horse. The method includes mounting a sensing surface of an accelerometer directly to one of hair and skin of a horse. The accelerometer detects respiratory structural vibration data. The horse is exercised. The respiratory structural vibration data is converted to a corresponding signal and the corresponding signal is wirelessly transmitted. The wirelessly transmitted corresponding signal is received at an audio generating device. The detected respiratory structural vibration data is stored, at least temporarily, in a memory. The audio generating device emits audible sound in real time based on the corresponding signal.

The present invention also comprises a method of monitoring interactions of physiological events of an exercising horse. The method includes placing a respiratory detection sensor and a second sensor proximate to the horse so as to move with the horse. The respiratory detection sensor detects and outputs detected respiratory data. The second sensor detects and outputs detected second sensor data. The second sensor is at least one of a lateral-axis angular rate sensor, a longitudinal-axis angular rate sensor, a vertical-axis angular rate sensor, an accelerometer, a speed sensor, an ECG electrode configuration set, an EMG sensor configuration set, an EEG sensor configuration set, EOG sensor configuration set, a ZPG sensor configuration set, a pressure sensor, a gas flow sensor, a gas detection sensor, a pH sensor, a temperature sensor, an imaging sensor, an optical sensor and a blood constituent sensor. The method further includes wirelessly receiving, at one of a trend display and a computer, the detected respiratory data and the detected second sensor data and displaying, on one of the trend display and the computer, the detected respiratory data and the detected second sensor data. The detected respiratory data and the detected second sensor data are synchronized with respect to time.

The present invention also comprises a method of monitoring interactions of physiological events of an exercising horse. The method includes placing a speed sensor and a second sensor proximate to the horse so as to move with the horse. The speed sensor detects and outputs at least one of detected raw data for calculating instantaneous speed and calculated instantaneous speed data. The second sensor detects and outputs detected second sensor data. The second sensor is at least one of a lateral-axis angular rate sensor, a longitudinal-axis angular rate sensor, a vertical-axis angular rate sensor, an accelerometer, a respiratory detection sensor, an ECG electrode configuration set, an EMG sensor configuration set, an EEG sensor configuration set, EOG sensor configuration set, a ZPG sensor configuration set, a pressure sensor, a gas flow sensor, a gas detection sensor, a pH sensor, a temperature sensor, an imaging sensor, an optical sensor and a blood constituent sensor. The method further includes wirelessly receiving, at one of a trend display and a computer, the detected second sensor data and at least one of detected raw data for calculating instantaneous speed and calculated instantaneous speed data and simultaneously displaying, on one of the trend display and the computer, the detected second sensor data and at least one of detected raw data for calculating instantaneous speed and calculated instantaneous speed data. The detected respiratory data and the detected second sensor data are synchronized with respect to time.

The present invention also comprises a method of monitoring interactions of physiological events of an exercising horse. The method includes mounting a lateral-axis angular rate sensor, a vertical-axis angular rate sensor and a speed sensor proximate to the horse so as to move with the horse. The lateral-axis angular rate sensor detects angular rotation data relative to the lateral-axis. The vertical-axis angular rate sensor detects angular rotation data relative to the vertical-axis. The speed sensor detects speed data of the horse. The method further includes mounting an electrocardiogram (ECG) electrode configuration set directly to the horse and mounting a sensing surface of a respiratory detection transducer directly to one of hair and skin of the horse. The ECG electrode configuration set detects ECG data. The respiratory detection transducer detects respiratory data. The method further includes exercising the horse and receiving, at one of a trend display and a computer, the detected angular rotation data relative to the lateral-axis, the detected angular rotation data relative to the vertical-axis, the detected speed data, the detected ECG data and the detected respiratory data. The method further includes displaying, on one of the trend display and the computer, the detected angular rotation data relative to the lateral-axis, the detected angular rotation data relative to the vertical-axis, the detected speed data, the detected ECG data and the detected respiratory data. The detected angular rotation data relative to the lateral-axis, the detected angular rotation data relative to the detected vertical-axis, the detected speed data, the detected ECG data and the detected respiratory data are synchronized with respect to time.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIGS. 20A-20E are screen shots of a trend display with a plurality of sensor trends synchronized in real time in accordance with preferred embodiments of the present invention;

FIGS. 22A-22D are screen shots of a trend display having angular-rate motion sensor trends, an accelerometer respiratory sensor trend and an electrocardiogram sensor trend synchronized in time in accordance with the preferred embodiments of the present invention;

FIG. 25 is a prior art dorsal (top-down) rendering of a skull of a horse showing locations of major bones of the skull; and FIG. 26 is a prior art ventral (bottom-up) rendering of a skull of a horse showing locations of major bones of the skull.

DETAILED DESCRIPTION OF THE INVENTION

Figure 1:
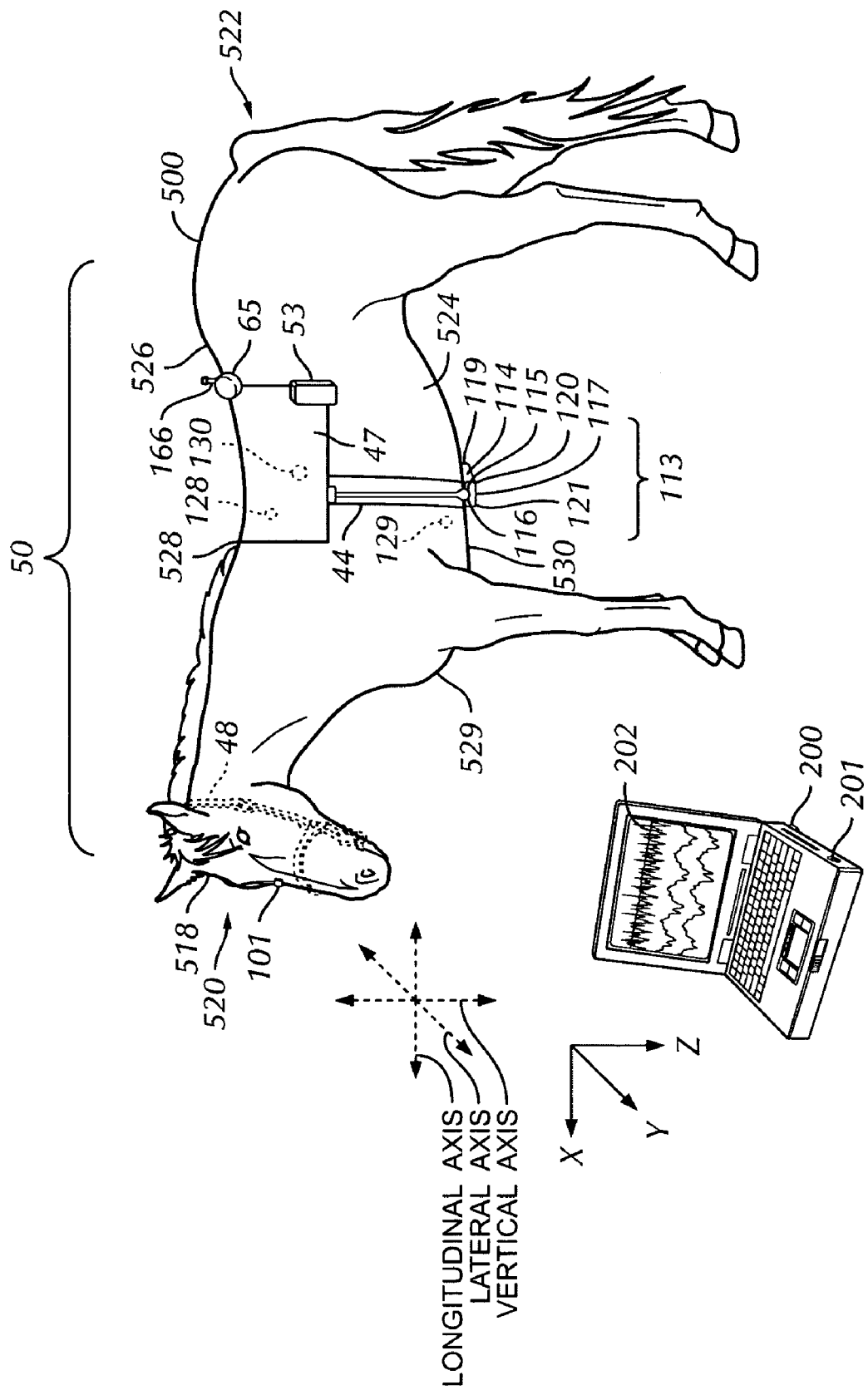
FIG. 1 a perspective view of a horse having a wireless equine physiological monitoring system in accordance with the preferred embodiments of the present invention mounted thereon.
Figure 2:
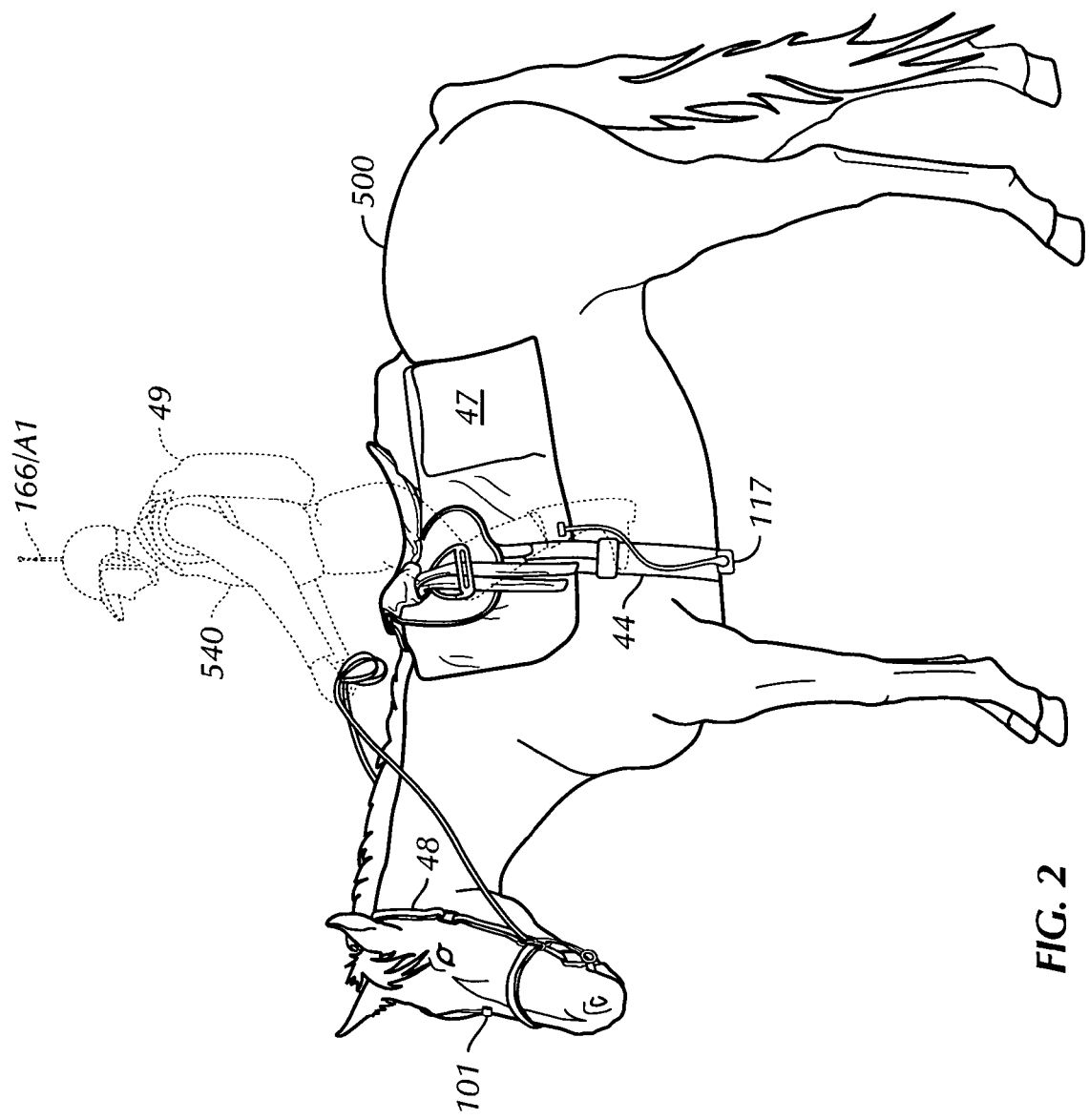
FIG. 2 is a perspective view of a horse having the wireless equine physiological monitoring system in accordance with the preferred embodiments of the present invention mounted thereon with a saddle pad with an on-board computer/controller mounted within the saddle pad.
Figure 3:
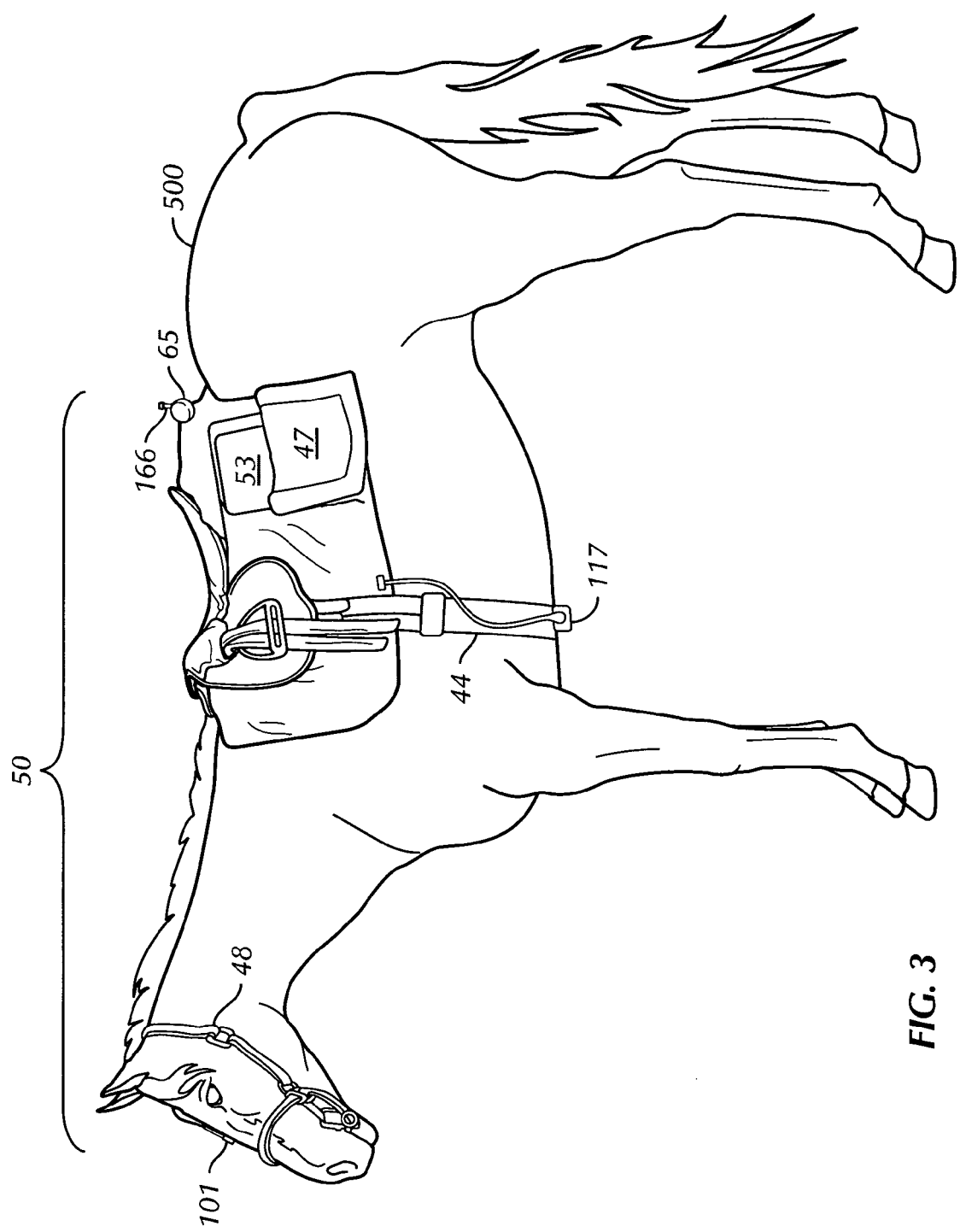
FIG. 3 is a side elevational view of a horse having the wireless equine physiological monitoring system in accordance with the preferred embodiments of the present invention mounted thereon with a an on-board computer/controller exposed.
Figure 4:
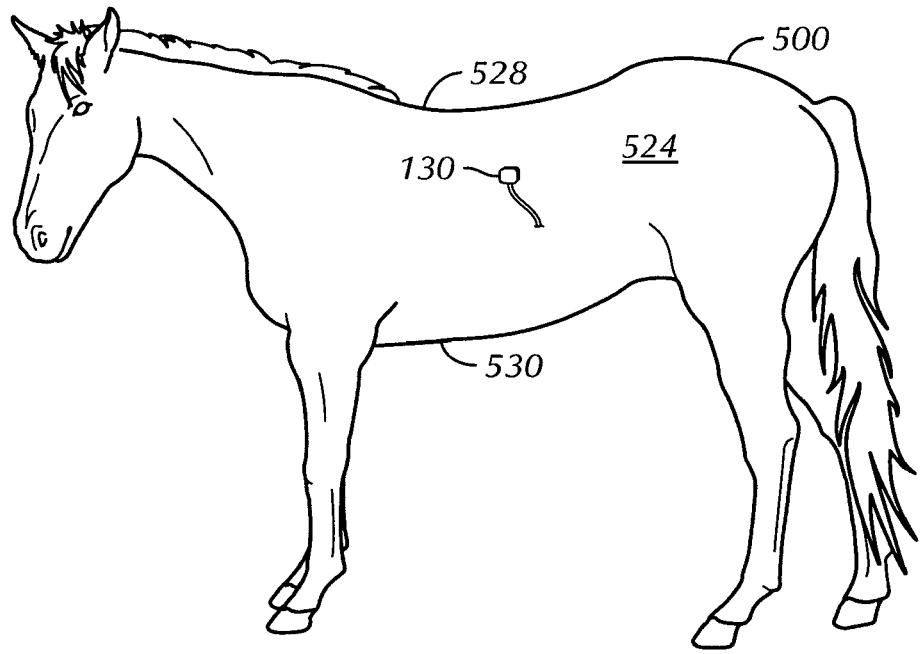
FIG. 4 is an enlarged side elevational view of a horse showing a speed accelerometer and mounting position therefor.

Certain terminology is used in the following description for convenience only and is not limiting. The words "right," and "left," "lower," and "upper" designate directions in the drawings to which reference is made. The words "inwardly" and "outwardly" refer to directions toward and away from, respectively, the geometric center of the object discussed and designated parts thereof. The terminology includes the words above specifically mentioned, derivatives thereof and words of similar import. Additionally, the words "a" and "an," as used in the claims and in the corresponding portions of the Specification, means "at least one."

For frame of reference, as used herein, FIG. 1 shows that a horse 500 has a cranial aspect 520, a caudal aspect 522, a left lateral side 524, a right lateral side 526, a dorsal aspect (top) 528 and a ventral aspect (bottom) 530. In three-dimensional space (X-axis, Y-axis, Z-axis), the horse 500 will be referenced as having a longitudinal-axis (X-axis), a lateral-axis (Y-axis) and a vertical-axis (Z-axis). The longitudinal-axis is defined through a length of the horse 500 as measured between the cranial and the caudal aspects 520, 522 of the horse 500. The lateral-axis is defined through a width of the body of the horse 500 as measured between the right and left lateral sides 524, 526 of the horse 500. The vertical-axis is defined through a height of the body of the horse 500 as measured between the dorsal aspect 528 and the ventral aspect 530 of the horse 500. This frame of reference establishing longitudinal, lateral and vertical axes (X, Y, Z) is relative and should not be construed as limiting. Any labels or orientations of (imaginary) axes may be utilized without departing from the present invention. In other words, tilting, shifting or rotating an axis or the frame of reference with respect to a horse 500 or ground is still within the scope of the invention. The horse 500 also includes a chest region 529 (FIG. 1). The locomotor system of the Horse 500 includes at least the musculoskeletal, neural and viscera systems.

Figure 23:
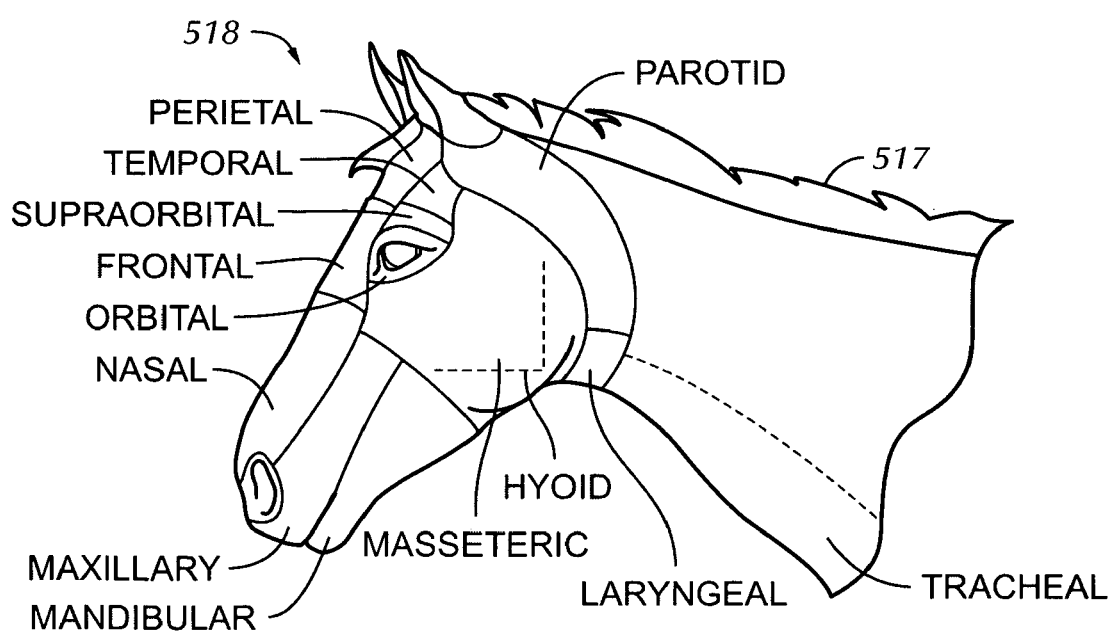
FIG. 23 is a prior art side elevational rendering of a head and neck of a horse depicting anatomical regions.
Figure 24:
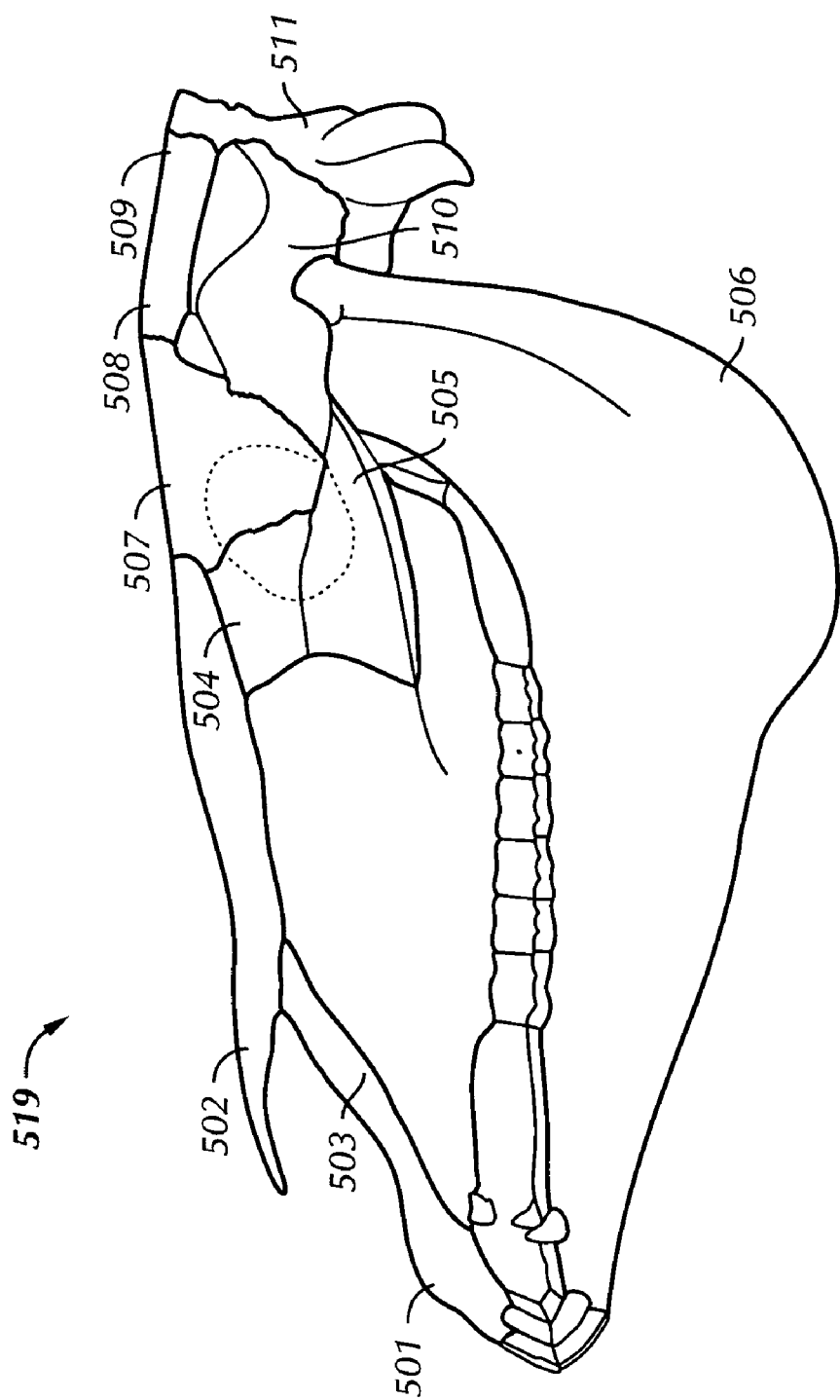
FIG. 24 is a prior art side elevational rendering of a skull of a horse showing locations of major bones of the skull.

FIG. 23 shows a prior art rendering of a head 518 and neck 517 of a horse 500 depicting anatomical regions. The anatomical regions include a maxillary region, a mandibular region, a masseteric region, a hyoid region, a laryngeal region, a tracheal region, a nasal region, a frontal region, an orbital region, a supraorbital region, a temporal region, a parietal region and a parotid region. Generally, the aforementioned regions correspond to the bone(s) and/or cartilage(s) in that region, underneath the hair and skin of the horse 500. FIGS. 24-26 are prior art renderings of a skull 519 of a horse 500 showing locations of major bones 501-515 of the skull 519. The skull 519 includes the following bones 501-515: incisive 501, nasal 502, maxilla 503, lacrimal 504, zygomatic 505, mandible 506, frontal 507, parietal 508, interparietal 509, temporal 510 (petrous and tympanic parts), temporal 510a (squamous part), occipital 511, vomer 512, sphenoid 513, pterygoid 514 and palatine 515.

Figure 5:
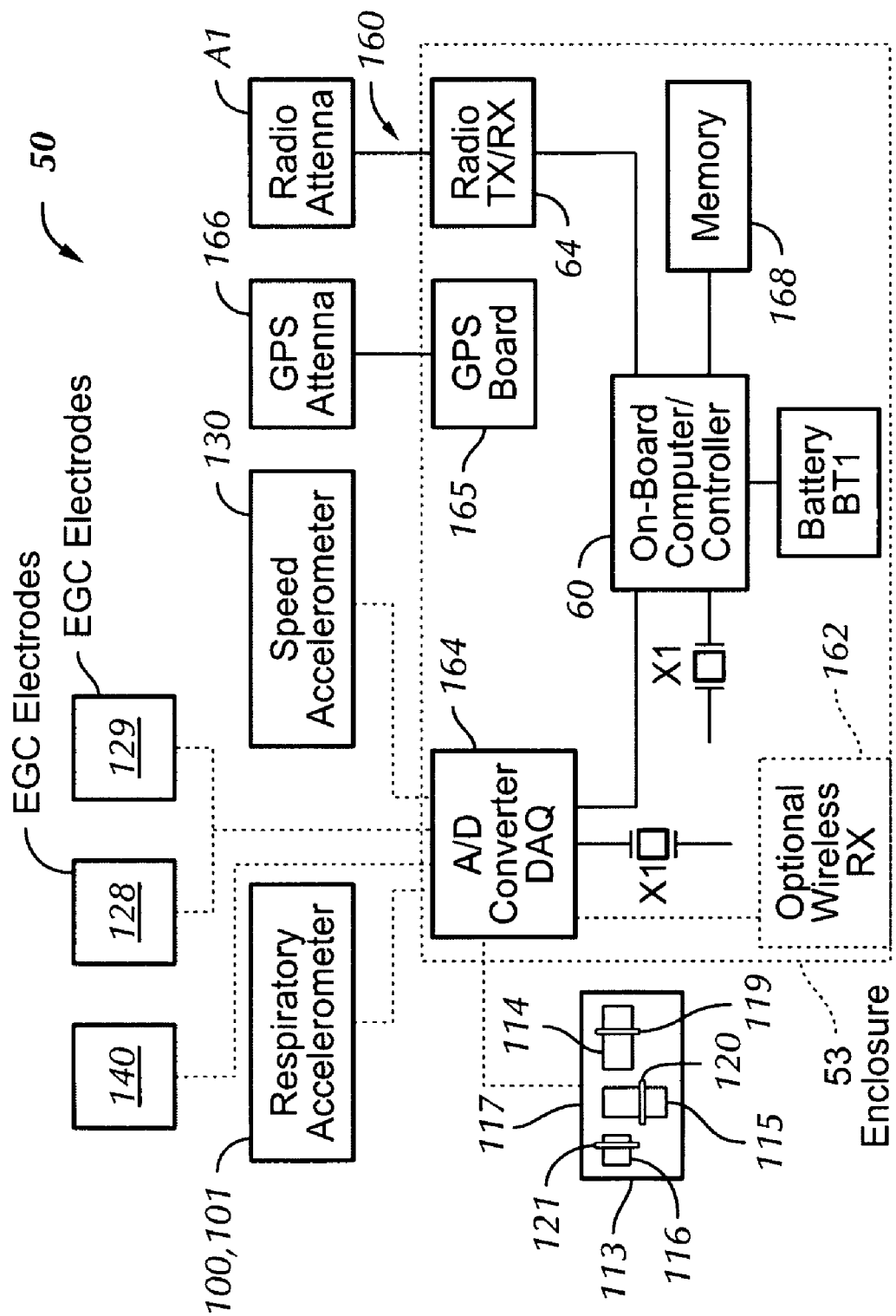
FIG. 5 is a schematic diagram depicting a wireless equine physiological monitoring system in accordance with a first preferred embodiment of the present invention.
Figure 9:
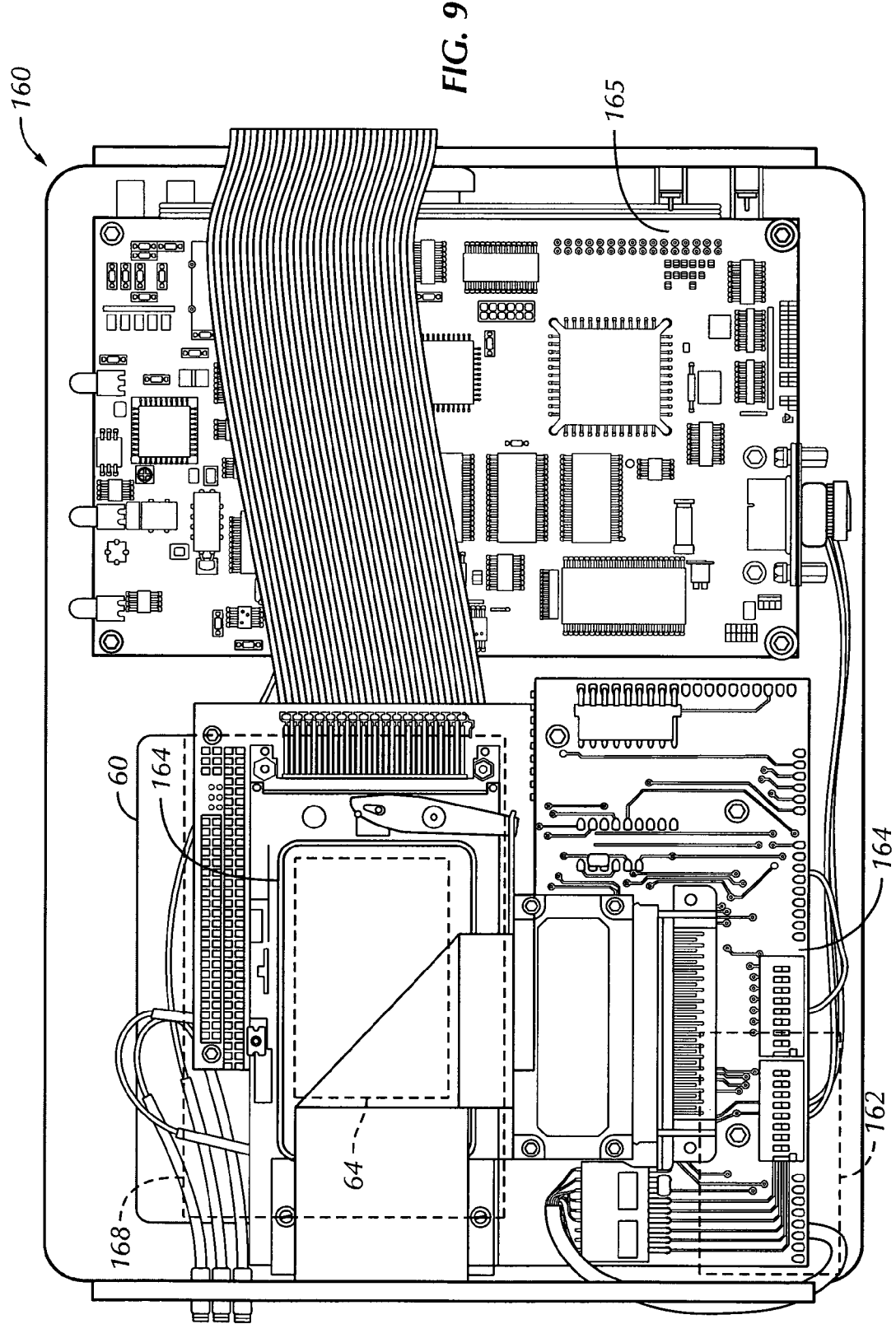
FIG. 9 is a top plan view of one possible implementation of the wireless monitoring system of FIG. 5.

Referring to the drawings in detail, FIGS. 1-5 show an equine physiological monitoring system 50 in accordance with a first preferred embodiment of the present invention. The equine physiological monitoring system 50 includes an on-board data acquisition control circuit 160 and a plurality of sensors 100, 101, 113, 114, 115, 116, 119, 120, 121, 128, 129, 130, 140, 165. FIG. 1 shows the placement of the equine physiological monitoring system 50 on a horse 500 with the location of each of the sensors 100 (FIGS. 11-12), 101, 113, 114, 115, 116, 119, 120, 121, 128, 129, 130, 140 (FIGS. 5-7), 165 (FIGS. 5 and 9).

The equine physiological monitoring system 50 is designed to be worn by the horse 500 while it is exercising with a rider 540 (phantom in FIG. 2), or while pulling a vehicle (not shown) such as a sulky or unencumbered by either. Alternately, components of the on-board data acquisition control circuit 160 and some or part of the plurality of sensors 100, 101, 113, 114, 115, 116, 119, 120, 121, 128, 129, 130, 140, 165, etc., can be worn by the rider/driver 540 or carried in a vehicle that the horse 500 is pulling. It is contemplated that the rider/driver 540 of the horse 500 may also be monitored while monitoring the horse 500 to document and/or observe the interactions between the rider/driver/vehicle and the horse 500.

It may also be desired that only the sensors 100, 101, 113, 114, 115, 116, 119, 120, 121, 128, 129, 130, 140, 165 are attached to the horse 500 and that all data is sent wirelessly to the on-board data acquisition control circuit 160, a remote host computer 200 or a trend display 202 (e.g., a laptop computer 200 running trending software that forms the trend display 202). For example, each of the plurality of sensors 100, 101, 113, 114, 115, 116, 119, 120, 121, 128, 129, 130, 140, 165 can be configured to have a wireless transmitter 104 (see e.g., FIG. 18) that transmits electromagnetic signals such as radiofrequency (RF) waves, Infrared (IR) or the like. Wirelessly transmitting sensor data may be less obtrusive on the horse 500 being monitored, even if the data is only wirelessly transmitted from the sensors 100, 101, 113, 114, 115, 116, 119, 120, 121, 128, 129, 130, 140, 165 to the on-board data acquisition control circuit 160.

Figure 17:
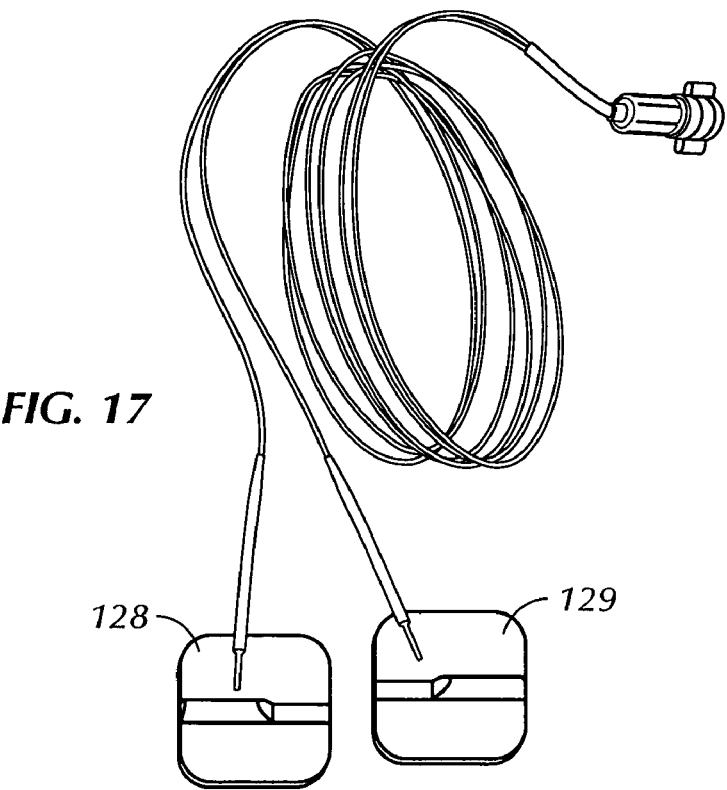
FIG. 17 is a top plan view of a dual-electrode electrocardiogram sensor in accordance with the preferred embodiments of the present invention.

The equine physiological monitoring system 50 includes one or more of a respiratory detection sensor 100, 101, a kinematic and kinetic motion sensor 113, an electrocardiogram (ECG) electrode configuration set 128, 129 and a speed sensor 130, 165. The equine physiological monitoring system 50 may also include a second sensor 140 (FIG. 5) configured to be mounted proximate to the horse 500. The second sensor 140 detects and outputs detected second sensor data. The second sensor 140 is at least one of a lateral-axis angular rate sensor 115, a longitudinal-axis angular rate sensor 114, a vertical-axis angular rate sensor 116, an accelerometer 119, 120, 121, a speed sensor 130, 165, (140), an ECG electrode configuration set 128, 129 (FIG. 17), an electromyography (EMG) sensor configuration set, an electroencephalograph (EEG) sensor configuration set, electrooculogram (EOG) sensor configuration set, an impedance pneumogram (ZPG) sensor configuration set, a pressure sensor, a gas flow sensor, a gas detection sensor, a pH sensor, a temperature sensor, an imaging sensor, an optical sensor and a blood constituent sensor.

The wireless equine physiological monitoring system 50 also includes the real-time trend display 202 (FIGS. 20A-20E, 21A-21B, and 22A-22D) that wirelessly receives the detected data from one or more of the sensors 100, 101, 113, 114, 115, 116, 119, 120, 121, 128, 129, 130, 140, 165. The trend display 202 displays the detected data with respect to time as the detected data is received (i.e., real-time trending). The detected respiratory data may also be stored (i.e., data-logging) in the on-board data acquisition control circuit 160 and/or at the host computer 200 and/or on a storage device for later review and analysis (i.e., historical trending). The trend display 202 may be a chart recorder. The recorder may be a paper chart recorder or a virtual chart recorder. The trend display 202 may be graphically displayed through a video display or a projector. The video display may be a liquid crystal display (LCD), a light emitting diode (LED) display, a cathode-ray tube (CRT) display and a plasma screen display.

Figure 15:
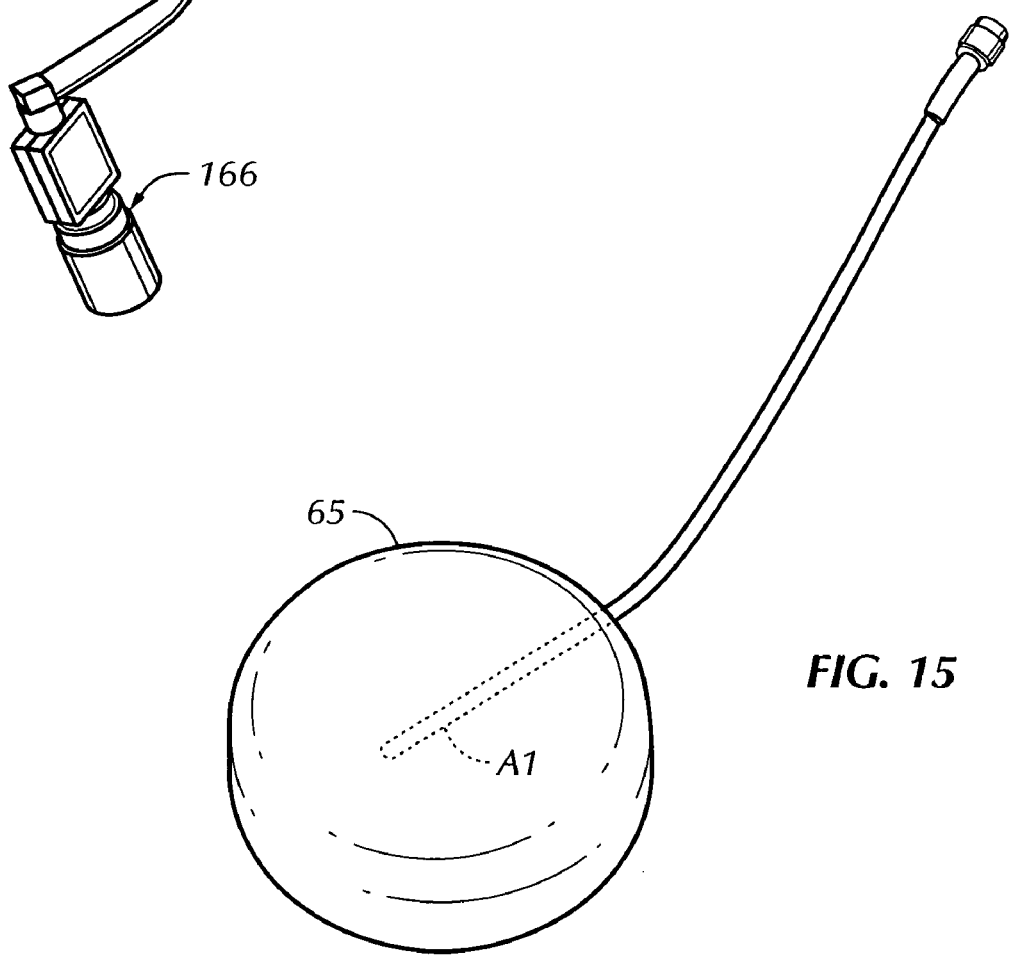
FIG. 15 is a perspective view of a radio antenna enclosure in accordance with the preferred embodiments of the present invention.

FIG. 5 is a schematic diagram depicting the wireless equine physiological monitoring system 50. The wireless equine physiological monitoring system 50 includes an enclosure 53 which houses the on-board data acquisition control circuit 160. The on-board data acquisition control circuit 160 includes an on-board computer/controller 60, a data acquisition (DAQ) system or card 164 (FIG. 9), a global positioning system (GPS) receiver board 165 (FIG. 9), a transmitter or transceiver 64 and a battery or other power source BT1. An external antenna A1 is coupled to the transceiver 64. FIG. 15 shows an enclosure 65 for the antenna A1. The on-board computer 60 may include a microprocessor, a memory storage device 168, random access memory (RAM) and typical connections such as keyboard, mouse, monitor, universal serial bus (USB), communications port and a network connection.

A prototype of the monitoring system 50 utilized a DAQ-Card-AI 16E-4 commercially available from National Instruments, Austin, Tex., connected to a model number PCM 9570 computer commercially from Advantech, Irvine, Calif. The DAQ card 164 includes signal conditioning circuitry for receiving a variety of different analog and/or digital signals at a plurality of different voltage and/or current levels. The DAQ card 164 may multiplex the signals through an analog to digital (A/D) converter and utilize serial, parallel, USB, Ethernet or any other communication medium to communicate the data acquired to the on-board computer/controller 60. These components are disposed in an enclosure 53, which can be situated in or on the saddle pad 47, a girth 44, a harness on the horse 500, a rider/driver 540, a cart, remotely or the like. Of course, a more simplified on-board data acquisition control circuit 160 or a dedicated local data logger may be used instead.

Preferably, the on-board data acquisition control circuit 160 has a clock X1 in either the DAQ card 164 or the on-board computer/controller 60 in order to synchronize acquired data with respect to time. Preferably, the clock X1 is a real time clock that can be calibrated and/or synchronized with another external clock, as necessary. Preferably, all data collected, displayed and/or stored is synchronized with respect to time. Preferably, the on-board data acquisition control circuit 160 has a real time clock X1 and the data is synchronized with respect to real time so that the data can be analyzed based on time events and/or can be synchronized with real time data from other sources.

Figure 6:
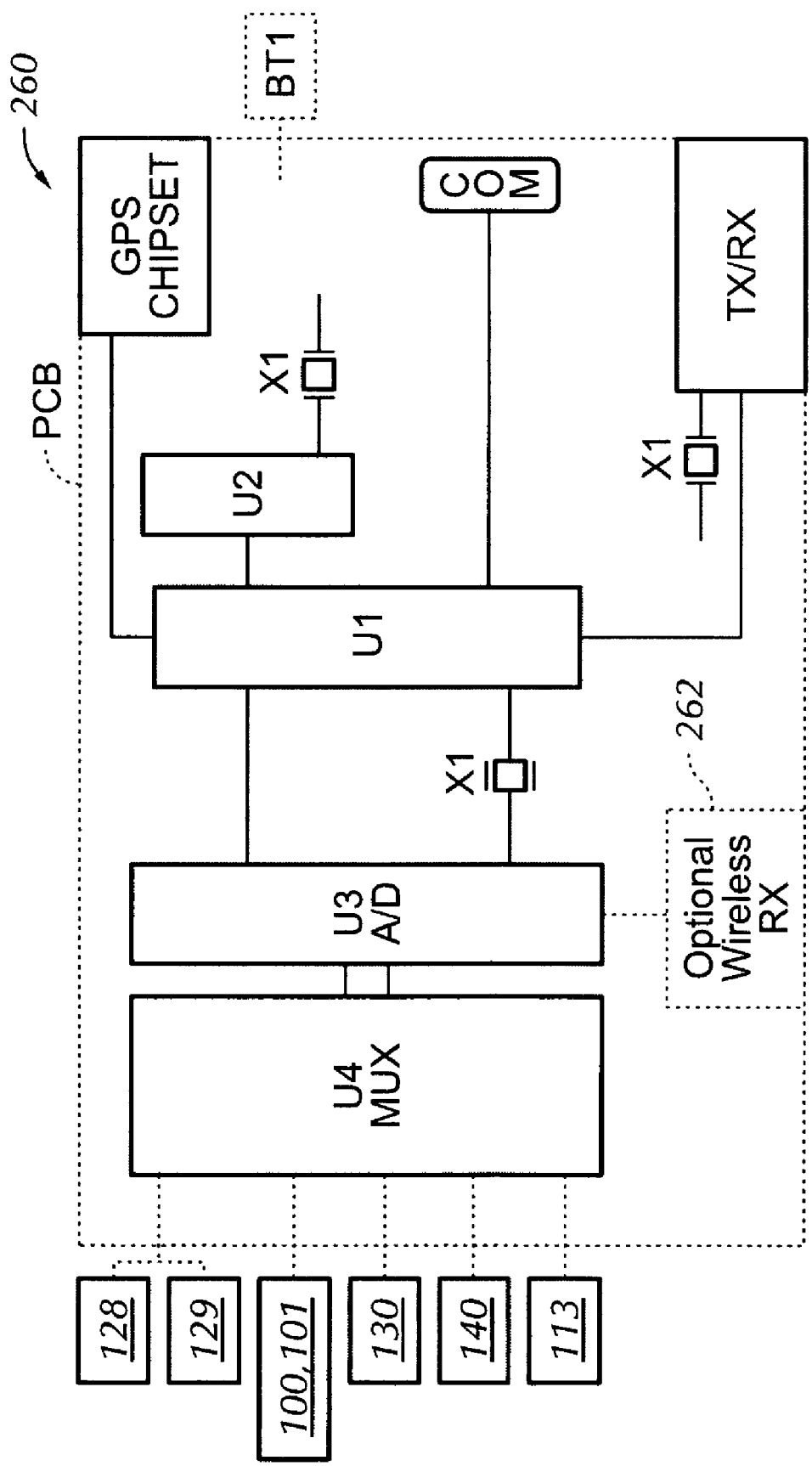
FIG. 6 is a schematic block diagram depicting a wireless equine physiological monitoring system in accordance with a second preferred embodiment of the present invention.
Figure 7:
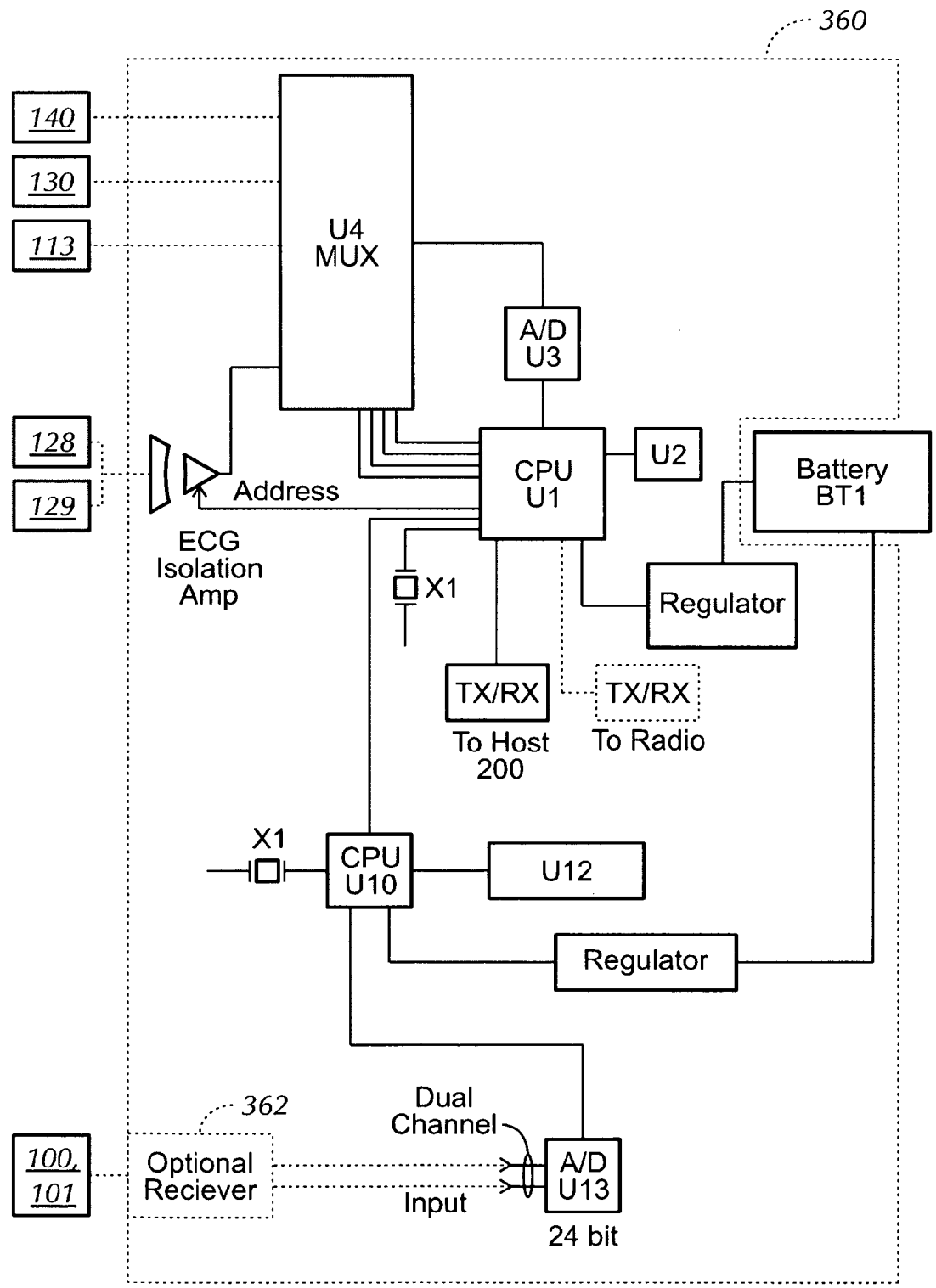
FIG. 7 is a schematic block diagram depicting a wireless equine physiological monitoring system in accordance with a third preferred embodiment of the present invention.

As shown in FIGS. 6-7, a dedicated control circuit 260, 360 can incorporate all of the functionality of the aforementioned DAQ card 164 and on-board computer/controller 60, and more, on one or more printed circuit boards (PCBs).

Each of the plurality of sensors 100, 101, 113, 114, 115, 116, 119, 120, 121, 128, 129, 130, 140, 165 are shown being coupled to the DAQ card 164, and the DAQ card 164 being coupled to the on-board computer/controller 60. However, one or more of the plurality of sensors 100, 101, 113, 114, 115, 116, 119, 120, 121, 128, 129, 130, 140, 165 maybe directly coupled to the on-board computer/controller 60. Preferably, each of the plurality of sensors 100, 101, 113, 114, 115, 116, 128, 129, 130, 140 has a built-in or a close-coupled wireless transmitter 104 (see FIG. 18) for sending data to the on-board data acquisition control circuit 160 wirelessly. For example, one or more sensors 100, 101, 113, 114, 115, 116, 128, 129, 130, 140 can be configured to transmit a wireless signal such as an IR, RF, Bluetooth or the like, using a wireless transmitter 104. Bluetooth is the registered trademark of Bluetooth SIG, Inc., Bellevue, Wash. Reducing the hard-wired connections between the sensors 100, 101, 113, 114, 115, 116, 128, 129, 130, 140 and the DAQ card 164 and on-board computer/controller 60 and/or eliminating the on-board data acquisition control circuit 160 makes it somewhat less intrusive on the subject horse 500 that is being monitored. Additionally, wirelessly transmitting sensor data makes it possible to monitor a horse 500, in real time, while the horse 500 is exercising.

The memory storage device 168 for the on-board data acquisition control circuit 160 may be a floppy disk drive, a CD read only memory (ROM) player/recorder, a tape player, a DVD player/recorder, a flash memory device such as a flash random access memory (flash-RAM) drive, a removable flash RAM or the like. The memory storage device 168 for the on-board data acquisition control circuit 160 may alternatively be a USB flash memory device (i.e., a USB memory key or a memory stick).

Optionally, the on-board data acquisition control circuit 160 also has input/output capability for video, wireless data I/O (e.g., WiFi), parallel, serial and multi-channel outputs. The on-board data acquisition control circuit 160 may receive data from video cameras, scanning devices or other more intelligent or complicated equipment in addition to and in conjunction with the sensor data.

Alternatively, the on-board data acquisition control circuit 160 may be implemented by a software program for a conventional personal digital assistant (PDA) that has wireless transmit/receive capabilities such as IR, Bluetooth, RF or the like. The PDA can be placed in a pouch on a saddle pad 47 or could be carried by a rider/driver 540 or held on the side-lines as the horse 500 is exercising. For example, the rider/driver 540 may wear a belt or backpack 49 for storing the on-board data acquisition control circuit 160.

The respiratory detection sensor 100 (FIGS. 11-12), 101 (FIGS. 1-3 and 10) may be a microphone or an accelerometer. A microphone is an electroacoustic transducer that responds to sound waves (acoustical waves) and outputs a corresponding electrical wave. An accelerometer 100, 101 senses an inertial reaction of a proof mass for measuring linear or angular acceleration. An accelerometer 100, 101 can detect and measure vibrations of a generally elastic or semi-elastic solid.

Preferably, the respiratory detection sensor 100, 101 is a respiratory vibration accelerometer 100, 101 that is responsive to equine respiratory structural vibrations.

Figure 10:
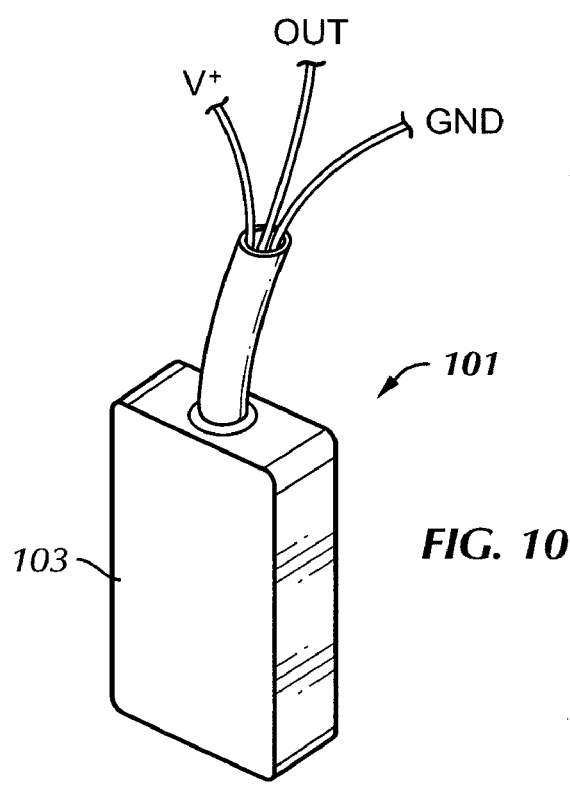
FIG. 10 is a perspective view of a sensing surface of a first respiratory vibration accelerometer/sensor in accordance with the preferred embodiments of the present invention.

FIG. 10 shows a first respiratory vibration accelerometer 101 in accordance with the preferred embodiments of the present invention. The first respiratory vibration accelerometer 101 is a piezoelectric accelerometer such as a piezoelectric crystal or a piezoelectric film accelerometer. The first respiratory vibration accelerometer 101 has a sensing surface 103 configured to be attached to one of hair, skin, bone, ligament, cartilage, and other tissue of a horse 500, such that the attachment is nearly an integral part of the hair, skin bone, ligament, cartilage, and other tissue. Preferably, the respiratory vibration accelerometer 101 includes an internal seismic mass or proof mass (not shown) that acts on a small element of piezo-polymeric film (not shown). The first respiratory vibration accelerometer 101 has lead wires for supply V+, output OUT and ground GND. Preferably, the respiratory vibration accelerometer 101 has a wide frequency response, good phase response and a relatively wide dynamic range. Preferably, the respiratory vibration accelerometer 101 has a frequency range of less than 2 Hz to about 20 KHz.

The raw voltage output from respiratory vibration accelerometer 100, 101 can be converted to engineering units by its calibration factor to read in mV/g, where g is approximately 9.8 meters/second-second (s2). Thus, the data can be quantified as the accelerations of the structures being sensed. Additionally, velocities and displacements of respiratory structural signals can be ascertained. From these data one may gain insights into the kinetics, kinematics, time functions, shapes, sizes or the like of respiratory structures. Preferably, data sensed by respiratory vibration accelerometer 100, 101 contains information relating to other body systems, e.g., the mechanics and locomotion of the horse 500 and cardiovascular events such as a cardiac rhythm and rate. These data can be separated from the parent data and their influences and interactions established.

The respiratory vibration accelerometer 100, 101 can be used in the study of varying ground and climatic conditions, genotypes, phenotypes, feeding and training strategies, influences of riders 540, drivers, or unencumbered by either, riding, driving equipment and training aids, pharmacological agents, medical and developmental histories, shoeing, metabolic, physiologic and psychological states, and intra and inter species communications and vocalizations.

Figure 11:
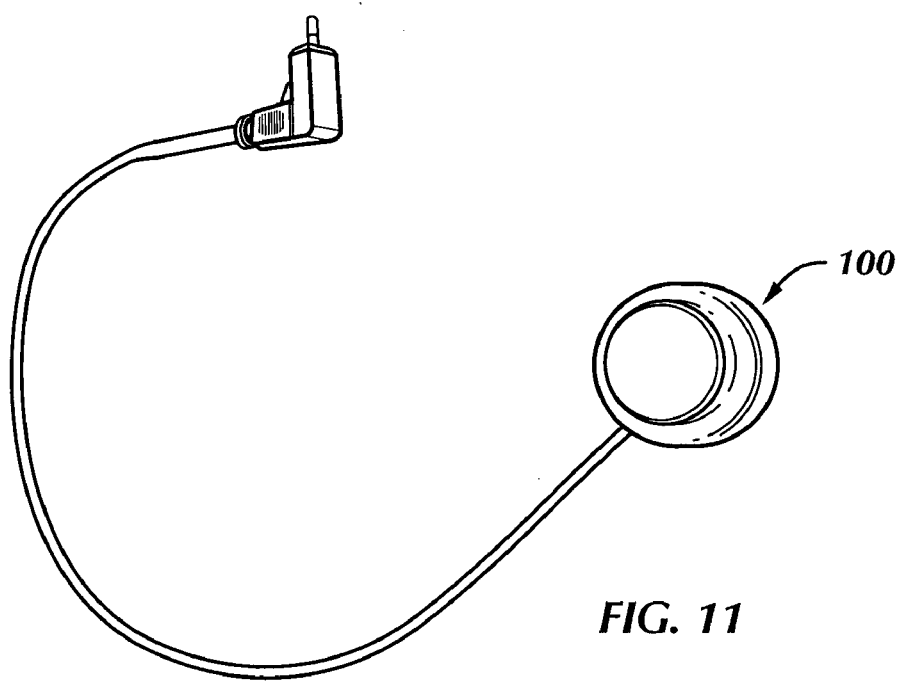
FIG. 11 is a top view of a second respiratory vibration accelerometer/sensor in accordance with the preferred embodiments of the present invention.
Figure 12:
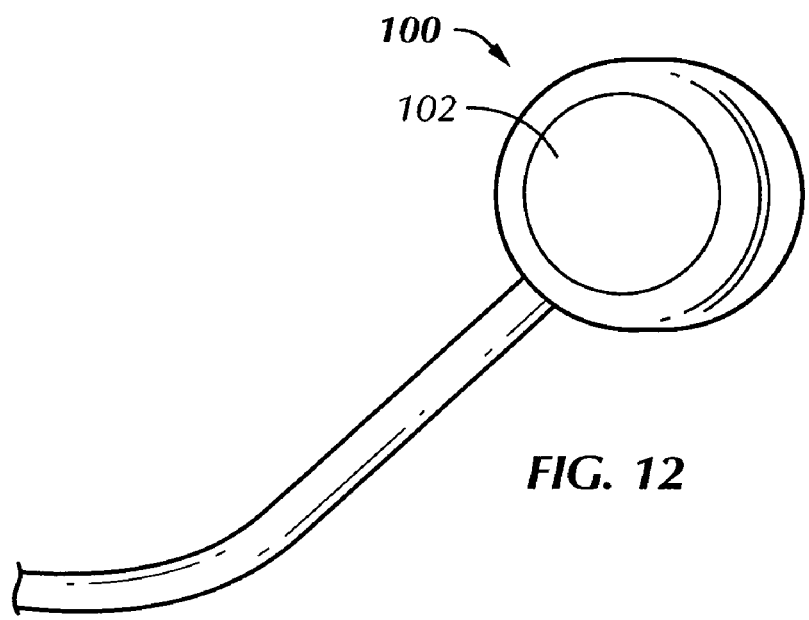
FIG. 12 is a perspective view of a sensing surface of the second respiratory vibration accelerometer/sensor of FIG. 11.

FIGS. 11-12 show a second respiratory vibration accelerometer 100 in accordance with the preferred embodiments of the present invention. Preferably, the vibration transducer 100 is an accelerometer such as a moving coil/mass-spring. Preferably, the accelerometer 100 is lightweight (e.g., about 13 grams). One preferred accelerometer is described in U.S. Pat. No. 5,461,193 (Schertler), the contents of which are incorporated by reference herein. The respiratory vibration accelerometer 100 includes a sensing surface 102 configured to be attached to one of hair, skin, bone, ligament, cartilage, and other tissue of a horse 500. The output from respiratory vibration accelerometer 100 can be quantified in a similar fashion as respiratory vibration accelerometer 101.

Other types of respiratory vibration accelerometers 100, 101 such as other configurations of a moving mass-spring accelerometer, a micro-electro-mechanical systems (MEMS) accelerometer, a micro-machined silicon accelerometer, another variety piezoelectric accelerometer, a potentiometric accelerometer, a linear variable differential transformer (LVDT) accelerometer, a fiber-optic accelerometer, a variable reluctance accelerometer and a variable capacitance accelerometer or the like can also be used for the same purpose.

Preferably, the sensing surface 102, 103 of the respiratory vibration accelerometer 100, 101 is affixed or attached using temporary adhesive, such as product number 34-3376 commercially available from National Starch and Chemical Co., Salisbury, N.C., directly to the skin overlying the nasal bones 502 of the horse 500 (i.e., the nasal region in FIG. 23). It is also anticipated that the respiratory vibration accelerometer 100, 101 can be bonded to the skin and/or hair using a liquid suture such as N-butlycyanoacrylate or Close commercially available from B. Braun Medical, Bethlehem, Pa., or other similar liquid suture product. It is important during the fixation process that the sensing surface 102, 103 of the respiratory vibration accelerometer 100, 101 be tightly adhered to the skin or hair of the horse 500, preferably without any air or liquid interface, such that the sensing surface 102, 103 of the respiratory vibration accelerometer 100, 101 is at least partially in direct contact with the skin or hair of the horse 500. This is accomplished by first removing any excessive hair with clippers and then prepping the desired area with alcohol to remove loose hair and debris. Next, the adhesive is applied to the outer circumference of the sensing surface 102, 103 of the respiratory vibration accelerometer 100, 101 which is then pressed onto the desired recording area. Thus, the respiratory vibration accelerometer 100, 101 is intimately attached to the hair or skin of the horse 500 so as to become a nearly integral component. The respiratory vibration accelerometer 100, 101 is responsive to respiratory structural vibrations of the horse 500 and outputs a signal corresponding to the respiratory structural vibrations.

The respiratory vibration accelerometer 100, 101 is preferably adhered, glued, epoxied or bonded directly to one of hair, skin, bone, ligament, cartilage, and other tissue of a horse 500. But, the respiratory vibration accelerometer 100, 101 may be mechanically coupled to one of hair, skin, bone, ligament, cartilage, and other tissue of a horse 500 or mechanically held in direct contact with one of hair, skin, bone, ligament, cartilage, and other tissue of a horse 500 without departing from the invention. It is contemplated that the respiratory vibration accelerometer 100, 101 can be attached directly to bone, cartilage or ligaments of the horse 500 by, for example, surgical implantation or the like.

In one embodiment, the sensing surface 102, 103 of the respiratory vibration accelerometer 100, 101 is adhered, glued, epoxied or bonded directly to attached to one of hair, skin, bone, ligament, cartilage, and other tissue of a horse 500 to create a vacuum condition between the sensing surface 102, 103 of the respiratory vibration accelerometer 100, 101 and the respective one of hair, skin, bone, ligament, cartilage, and other tissue of the horse 500.

It is further contemplated that the respiratory vibration accelerometer 100, 101 can be mounted inside the head 518 of the horse 500.

Preferably, the nasal region is chosen because respiratory structural vibrations readily pass into the nasal bones 502 underlying the skin and through the skin in this area and thus are detected quite easily by the respiratory vibration accelerometer 100, 101. Other sites of attachment for the respiratory vibration accelerometer 100, 101 include, but are not limited to, the hair and/or skin overlying the nasal turbinates, the larynx, the trachea, maxillary region, the masseteric region, the hyoid region (i.e., the ventral portion of the hyoid apparatus), the laryngeal region, the tracheal region, the frontal region, the orbital region, the supraorbital region, the chest region 529, the temporal region, the parietal region, the parotid region, or the like. These alternate sites of attachment also allow for the detection of different types and levels of vibrations. Further, respiratory vibration accelerometers 100, 101 configured in different ways can also enhance the detection of types and levels of vibrations. Thus, as the horse 500 exercises, the respiratory structural vibrations are sensed by the respiratory vibration accelerometer 100, 101 and the resulting electrical impulses pass via a cable or wirelessly to the DAQ card 164.

Figure 8:
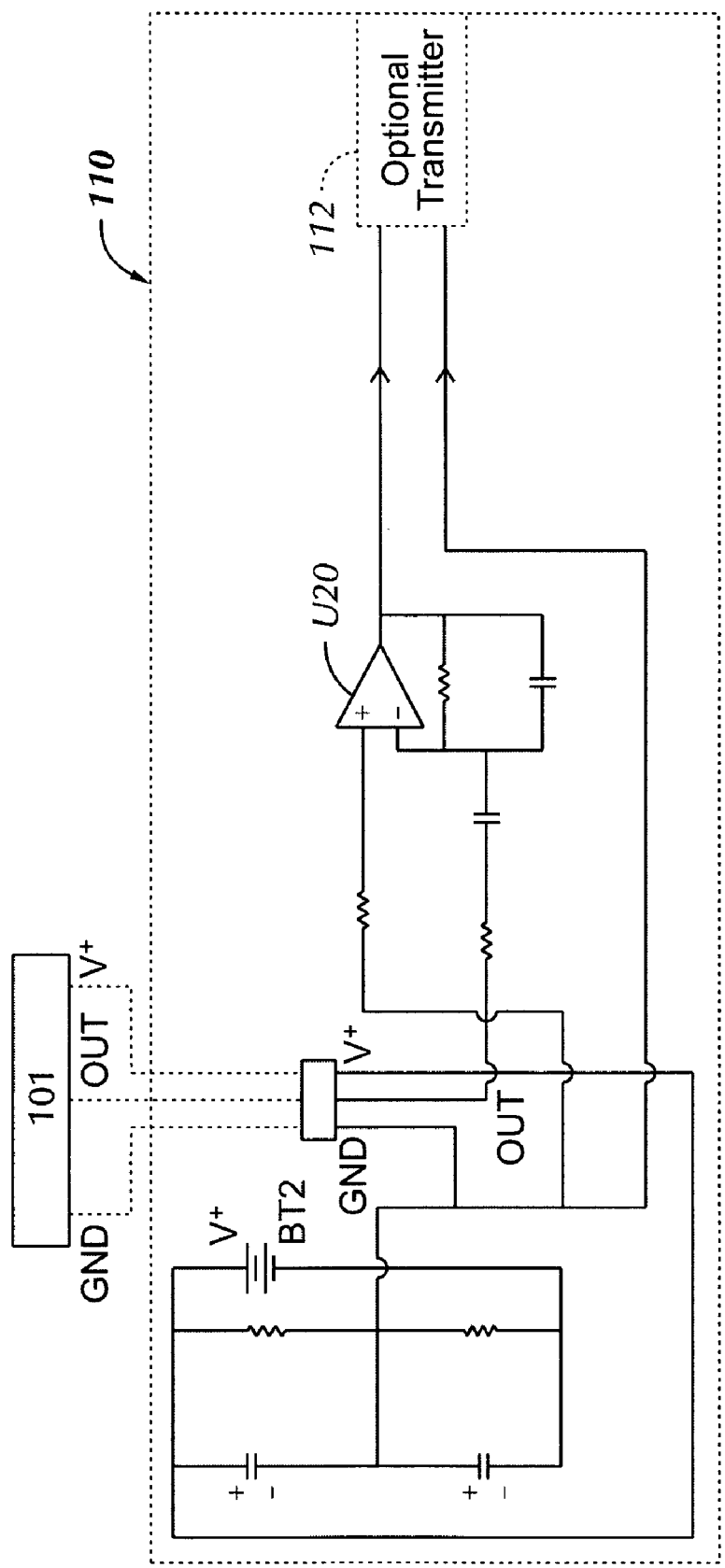
FIG. 8 is a schematic block diagram depicting a respiratory structural vibration accelerometer control circuit in accordance with preferred embodiments of the present invention.

FIG. 8 is a schematic block diagram of an accelerometer control circuit 110 in accordance with preferred embodiments of the present invention. The accelerometer control circuit 110 includes a battery or other power source BT2, an amplifier U20 and suitable biasing components, such as resistors and capacitors, for supplying a voltage signal to the respiratory vibration accelerometer 101, if necessary, and for receiving a data signal from the respiratory vibration accelerometer 101 in order to send data. The accelerometer control circuit 110 is particularly designed for the respiratory vibration accelerometer 101, but a similar accelerometer control circuit 110 can be utilized for the respiratory vibration accelerometer 100. The primary difference between the first respiratory vibration accelerometer 100 and the second respiratory vibration accelerometer 101 is that the second respiratory vibration accelerometer 101 requires supply power V+ while the first respiratory vibration accelerometer 100 does not.

Optionally, the accelerometer control circuit 110 includes a wireless transmitter 112 configured to transmit data. Preferably, the wireless transmitter 112 is configured to transmit frequencies as low as a few hertz (Hz). Sensing, recording and storing frequencies in the less than or equal to 2 Hz to 200 Hz range is of interest in order to fully appreciate respiratory structural vibrations. Generally, commercially available wireless transmitter/receiver units and recording units are not designed to address these frequencies in an accurate manner, if at all. Preferably, the various embodiments of the present invention accurately sense, record and store respiratory vibration data from less than or equal to 2 Hz to greater than or equal to 10 kHz.

Figure 18:
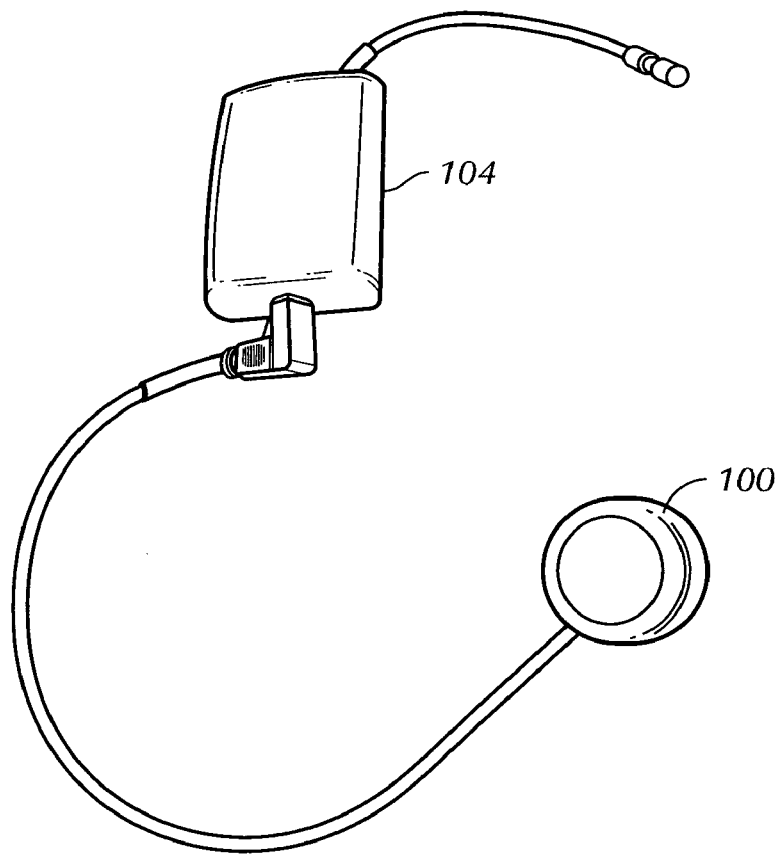
FIG. 18 is a perspective view of a wireless sensor transmitter attached to the respiratory vibration accelerometer/sensor of FIG. 11.

The respiratory vibration accelerometer 100, 101 may be hardwired or wired directly to the control circuit 160 or the control circuit 160 may include an optional wireless receiver 162 for receiving data wirelessly from the optional wireless transmitter 112 of the respiratory vibration accelerometer control circuit 110. Alternatively, as shown in FIG. 18, the respiratory vibration accelerometer 100, 101 can be attached to a wireless transmitter 104, affixed directly to the horse 500 by glue, adhesive, or the like or affixed by a clip and/or strap to a mane of the horse, a bridle, a halter 48 or other device of the horse 500, with a corresponding wireless receiver. The corresponding receiver is electrically connected to the DAQ card 164. This arrangement negates the need for cable to be strung from the respiratory vibration accelerometer 100, 101 on the head 518 of the horse 500 along the neck 517 to the DAQ card 164. It is anticipated that other types of wireless transmitters/receiver combinations using any frequency and any communication protocol that is minimally susceptible to noise can be used for the same purpose.

Figure 13:
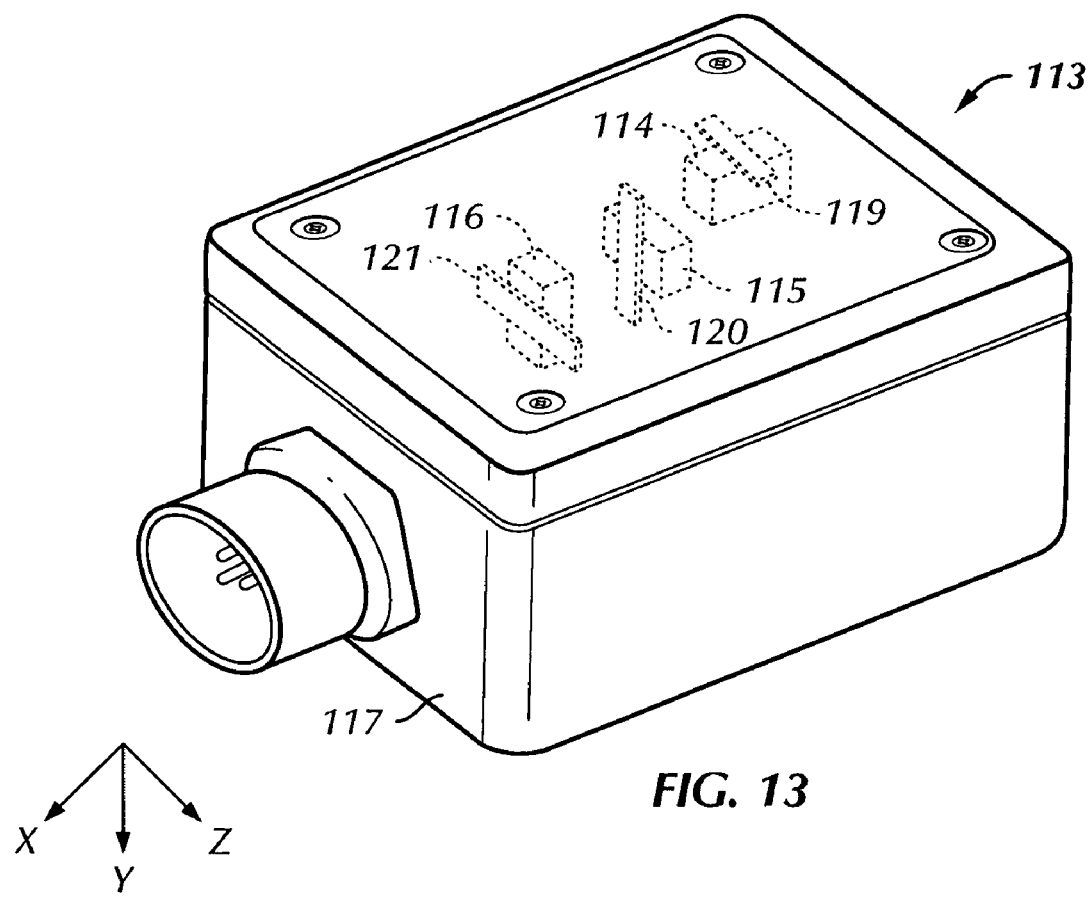
FIG. 13 is perspective view of a combined lateral-axis and vertical-axis angular rate sensors in accordance with the preferred embodiments of the present invention.
Figure 14:
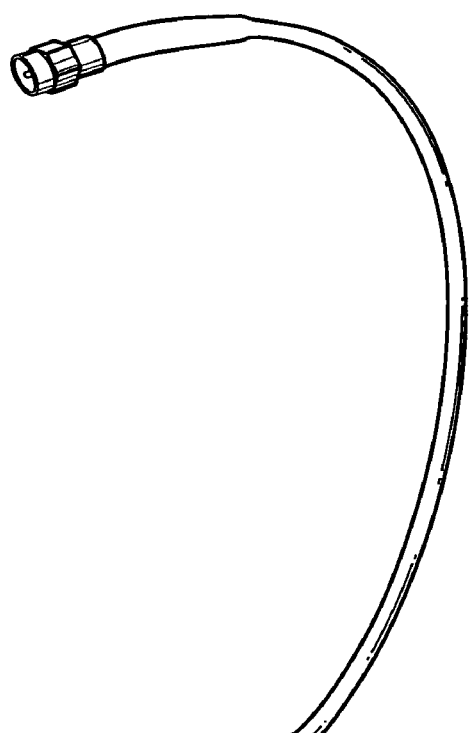
FIG. 14 is a perspective view of a GPS antenna for use with various preferred embodiments of the present invention.

FIGS. 1 and 13 show the motion sensor 113 that senses equine motion in multi-dimensional space (X, Y, Z). The kinematic and kinetic motion sensor 113 includes at least one angular rate sensor 114, 115, 116 and at least one accelerometer 119, 120, 121. The at least one angular rate sensor 114, 115, 116 and the at least one accelerometer 119, 120, 121 are configured to be mounted proximate to a horse 500 so as to move with the horse 500. The at least one angular rate sensor 114, 115, 116 detects angular rotation data relative to a first-axis. The at least one accelerometer 119, 120, 121 is mounted proximate to the at least one angular rate sensor 114, 115, 116 and is generally orthogonal to the first-axis. Preferably, the motion sensor 113 includes a first-axis angular rate sensor 114, a second-axis angular rate sensor 115 and the third-axis angular rate sensor 116 and a first accelerometer 119, a second accelerometer 120 and a third accelerometer 121, respectively. The first-axis angular rate sensor 114, the second-axis angular rate sensor 115 and the third-axis angular rate sensor 116 and the first accelerometer 119, the second accelerometer 120 and the third accelerometer 121 are all configured to be mounted proximate to the horse 500 so as to move with the horse 500. The first-axis angular rate sensor 114 detects angular rotation data relative to the first-axis, and the first accelerometer 119 is mounted proximate to the first-axis angular rate sensor 114 and is disposed orthogonal to the first-axis. The second-axis angular rate sensor 115 detects angular rotation data relative to the second-axis, and the second accelerometer 120 is mounted proximate to the second-axis angular rate sensor 115 and is disposed orthogonal to the second-axis. The third-axis angular rate sensor 116 detects angular rotation data relative to the third-axis, and the third accelerometer 121 is mounted proximate to the third-axis angular rate sensor 116 and is disposed orthogonal to the third-axis.

The first-axis is one of the lateral-axis, the vertical-axis and the longitudinal-axis, the second-axis is one of the other of the lateral-axis, the vertical-axis and the longitudinal-axis and the third-axis is the remaining one of the other of the lateral-axis, the vertical-axis and the longitudinal-axis. The kinematic and kinetic motion sensor 113 could be implemented with only one of the first-axis angular rate sensor 114, the second-axis angular rate sensor 115 and third-axis angular rate sensor 116. Thus, the angular rate sensors 114, 115, 116 are mounted mutually orthogonal to each other. Optionally, additional angular rate sensors 114, 115, 116 and/or additional accelerometers 119, 120, 121 can be provided in the motion sensor 113 that are aligned with other axes. The motion sensor 113 may be implemented with other sensor technologies in addition to or in replacement of angular rate sensors 114, 115, 116 and/or accelerometers 119, 120, 121.

The motion sensor 113 that includes at least one of an angular rate sensor 114, 115, 116 and at least one accelerometer 119, 120, 121, as described in the various embodiments herein, senses phase shifts of the respiratory locomotor coupling relationship exhibited by the exercising horse 500. The accelerometer(s) 119, 120, 121 within the motion sensor 113 allows for the estimation of the metabolic energy expenditure that occurs during the respiratory locomotor phase shifts. Further, the various configurations of the angular rate sensors 114, 115, 116 and accelerometers 119, 120, 121 sense the variations in movements of the horse 500 due to respiratory mechanics, metabolic energy expenditure, speed of movement, cardiovascular events or the like. The motion sensor 113 is configured to output multi-dimensional motion data of the horse 500.

The motion sensor 113 can be used in the study of varying ground and climatic conditions, genotypes, phenotypes, feeding and training strategies, influences of riders 540, drivers, or unencumbered by either, riding, driving equipment and training aids, pharmacological agents, medical and developmental histories, shoeing, metabolic, physiologic and psychological states, and intra and inter species communications and vocalizations.

The trend display 202 displays the detected angular rotation data relative to at least one of the first-axis, the second-axis and the third-axis rotation data with respect to time as the detected angular rotation data relative to the single-axis is received (i.e., real-time trending). The detected angular rotation data relative to at least one of the first-axis, the second-axis and the third-axis rotation data with respect to time may also be stored in the on-board data acquisition control circuit 160 and/or at the host computer 200 and/or on a storage device 168, 206 for later review and analysis (i.e., historical trending).

Preferably, the kinematic and kinetic motion sensor 113 is enclosed within a small enclosure 117 that is then mounted onto a girth 44 (i.e., a strap overlying the ventral side 530 of the horse 500). This area is chosen because it is in the central plane, and close to the center of mass of the horse 500. The kinematic and kinetic motion sensor 113 may also be mounted or affixed directly to the hair or skin of the horse 500. However, the kinematic and kinetic motion sensor 113 can be mounted in other locations on or near the horse 500 without departing from the present invention. The signals generated by the angular rate sensors 114, 115, 116 and the accelerometers 119, 120, 121 pass by cable to the DAQ card 164 and then to the on-board computer/controller 60. Optionally, a wireless transmitter is built into the kinematic and kinetic motion sensor 113 enabling the kinematic and kinetic motion sensor 113 to communicate data wirelessly to the on-board data acquisition control circuit 160 and/or to the host computer 200 and/or to the trend display 202.

Real time viewing of the graphed signals allows the observer to immediately discern basic locomotor parameters that help in elucidating the interrelationships among body systems of the horse 500. For example, for each gait type and stride, there is a unique and distinct rotation of the horse 500 around the lateral-axis (pitch) that is detected by the "Y" sensor 114, 115, 116. From the waveform that is generated one can deduce the gait (i.e., walk, trot, pace, canter or gallop), the stride frequency and phase of the stride (i.e., stance or suspension). The "Z" sensor 114, 115, 116 measures the distinct rotations of a gait type and stride around the vertical-axis (yaw) the waveform from which strengthens the deduction of type of gait, stride frequency, and is particularly useful in determining gait phase (i.e., right versus left lead for canter and gallop or right versus left diagonal for the trot). With these types of basic observations and more extensive analysis, one can better appreciate the synergies that exist in the exercising horse 500.

The ECG electrode configuration set 128, 129 includes at least two self-adhering electrodes 128, 129 such as product number 664 commercially available from Uni-Patch, Wabasha Minn. The ECG electrode configuration set 128, 129 may include a plurality of electrodes 128, 129. The ECG electrode configuration set 128, 129 is used for obtaining the electrocardiogram. The ECG electrodes 128, 129 are configured in a Base-Apex lead system, which is the most common method of recording exercising ECGs of horses 500. There are many other types of ECG electrodes that can be used for the same purpose. As shown in FIG. 1, the ECG electrodes 128, 129 are situated under the saddle pad 47 and a girth 44, next to the skin and held in place by adhesive. Prior to placement, the electrode attachment sites on the horse 500 are prepped with alcohol to remove debris that could interfere with detection of the ECG. The electrical signals generated by the ECG electrodes 128, 129 pass via cable to the data acquisition board (DAQ) 164 and then to the on-board computer/controller 60.

Any number of additional ECG electrodes 128, 129 can be utilized without departing from the present invention. It is anticipated that more than two electrodes 128, 129 are used to record the ECG waveform. The ECG is used to detect cardiac rhythm and rate. Further, use of the time synchronization function of the system allows for precise comparison of cardiac data with the respiratory locomotor events and speed. For example, some types of cardiac arrhythmias can change respiratory and locomotor patterns of exercising horses 500. In addition, some cardiac rhythm disturbances may only occur at a particular speed or metabolic state.

Figure 19:
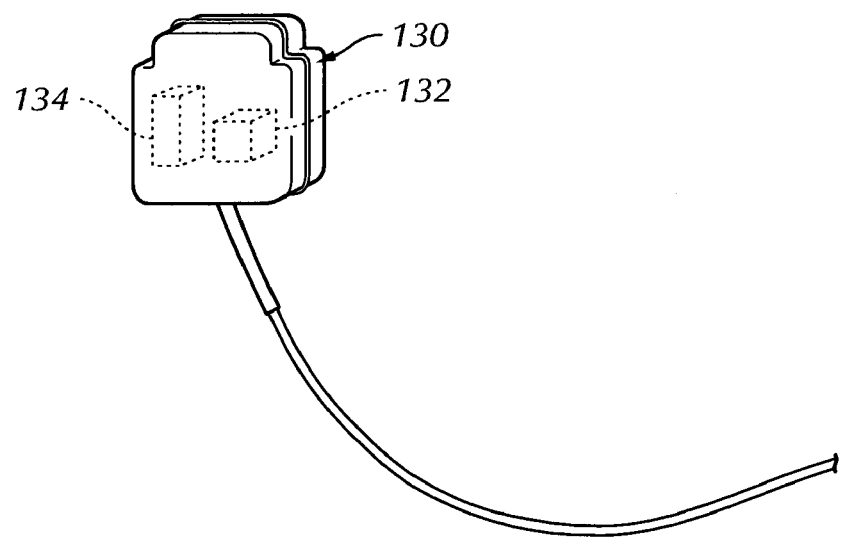
FIG. 19 is a bottom plan view of a speed accelerometer and associated circuitry in accordance with the preferred embodiments of the present invention.

The equine physiological monitoring system 50 also includes a speed sensor 130 that senses equine speed. The speed sensor or transducer 130 (FIG. 19) is, in one embodiment, an accelerometer 132 that detects acceleration and deceleration in a longitudinal-axis of a horse 500. The speed sensor 130 is configured to be mounted proximate to the horse 500. Preferably, the speed sensor 130 is mounted in the longitudinal-axis on one of the lateral sides 524, 526 of the horse 500 and is firmly adhered to the skin/hair of the horse 500 with temporary adhesive. The speed sensor 130 is connected by cable to the DAQ card 164. Thus, the speed sensor 130 is used to measure the overall accelerations and decelerations of the horse 500 in the horizontal plane. Preferably, the speed sensor 130 yields a positive signal output when the horse 500 is moving in the forward direction. When the acceleration signal is integrated over time (i.e., mathematical integral) it yields the speed of the horse 500. Optionally, a lateral-axis angular rate sensor 134 is mounted proximate to the speed accelerometer 130. The lateral-axis angular rate sensor 134 detects angular rotation data relative to the lateral-axis of the horse 500. The lateral-axis angular rate sensor 134 provides compensation for slippage in placement or changes in orientation of the speed accelerometer 132 with respect to the horse 500 and relative to the ground.

An alternative method of obtaining the speed of the horse 500 utilizes Global Positioning System (GPS) technology. The system includes a GPS receiver board 165 (FIG. 9) incorporated into the enclosure 53 with its output signal cable attached to the data acquisition board (not shown). The GPS receiver board 165 receives GPS data from GPS satellites. The GPS receiver board 165 updates GPS data more than once per second. Preferably, the GPS receiver board 165 updates at least five (5) times per second. The GPS receiver board 165 is configured to perform at least one of outputting data proportional to speed and calculating speed of the horse 500 from the updated GPS data. Thus, the GPS receiver board 165 may itself calculate speed from the received GPS data, or the GPS receiver board 165 may simply output raw data from which the speed can be calculated by the on-board data acquisition control circuit 160 or by the remote host computer 200, for example.

Figure 16:
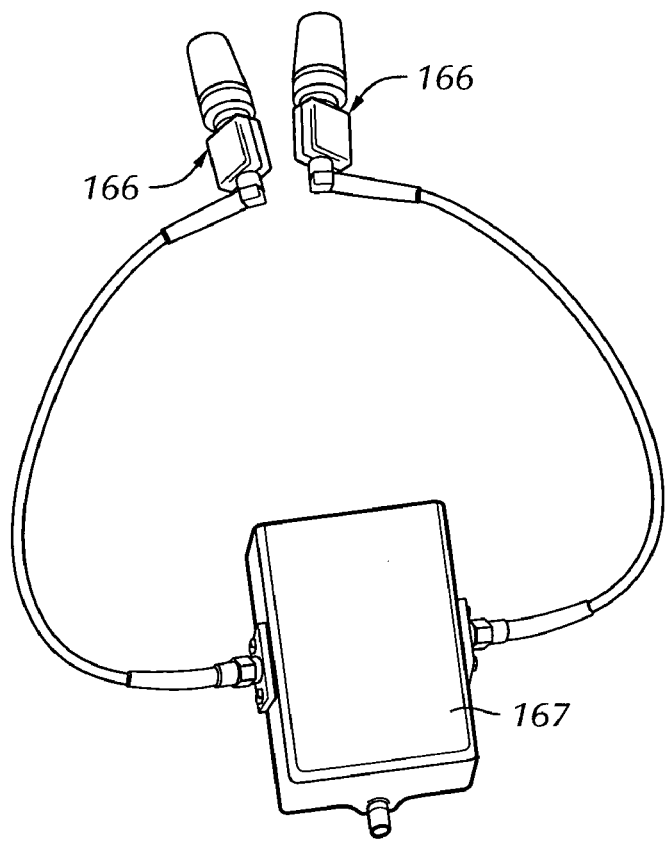
FIG. 16 is a perspective view of a dual-antenna splitting device in accordance with the preferred embodiments of the present invention, shown with two GPS antennas attached.

Since it is known from high speed video filming of running horses 500 that speed fluctuations within a single stride can be as much as five (5) miles per hour (MPH) or greater, frequent updates of a GPS system is desirable in order to more accurately measure stride components, respiratory, locomotor and cardiac events. A GPS receiver board 165 (FIG. 9) may be an "Invicta 210" commercially available from Raven Industries, Sioux Falls, S. Dak. The GPS antenna 166 is mounted on the top back portion of the saddle pad 47. Alternatively, the GPS antenna 166 can be mounted in other locations such as other parts of the horse 500 or on the rider 540 or on the cart/sulky or the like. The Invicta GPS receiver board 165 outputs a signal that is proportional to speed ten (10) times per second (i.e., about 45 Hz per mile per hour). There are other manufacturers of GPS boards that update more than once per second. FIG. 16 shows a dual-antenna splitting device 167 in accordance with the preferred embodiments of the present invention, having two GPS antennas 165 attached thereto for improving reception.

An alternative method of obtaining the speed of the horse 500 utilizes at least one Doppler transceiver that transmits an electromagnetic signal and receives a reflected or transponded version of the electromagnetic signal. The electromagnetic signal may be a radar signal, a microwave signal, an infrared signal or the like. The signal may also be an ultrasonic signal without departing from the invention. The Doppler transceiver is configured to be mounted proximate to a horse 500 so as to move with the horse 500. The Doppler transceiver is configured to perform one of outputting data proportional to speed and calculating speed of the horse 500 based on the difference in time/frequency between the transmitted and received electromagnetic signal. Preferably, at least one compensation transceiver is mounted in conjunction with the Doppler transceiver. The compensation transceiver also transmits an electromagnetic signal and receives a reflected or transponded version of the electromagnetic signal. The compensation transceiver is configured to mount in an opposite orientation as compared to the Doppler transceiver, and the compensation transceiver is configured to compensate the Doppler transceiver for uneven surface conditions and/or movements of the horse 500 based on the difference in time/frequency between the transmitted and received electromagnetic signal.

The resulting data that is generated from the respiratory vibration accelerometer 100, 101, the motion sensor 113, the ECG electrode configuration set 128, 129, and the speed accelerometer 130 (and/or the GPS receiver board 165) are collected and stored in the memory 168 of the on-board data acquisition control circuit 160. In the first preferred embodiment, this data acquisition process as well as all subsequent processes are performed using a commercial software program such as LABVIEW 6.x, commercially available from National Instruments, Austin, Tex. Other software packages and display or trending techniques can be utilized. For example, dedicated paper or paperless (virtual) chart recorders or dedicated displays in general may be used in lieu of, or in addition to, a host computer 200. Preferably, each data point displayed or logged is time synchronized, so as to permit an overall analysis of what happens or happened at any given point in time (i.e., real time or historical look back). Custom control and/or display software can also be utilized as a user interface without departing from the present invention.

Simultaneously to the data being stored or logged in the memory 168 of the on-board data acquisition control circuit 160, the data is also transmitted via the transceiver 64 by radio signal. For example, the transceiver can be a product number AIR-LMC352, commercially available from Cisco Systems, San Jose, Calif. The transceiver 64 is connected to the on-board computer/controller 60 and transmits data via an antenna(s) A1 to the host computer 200 which also has a similar transceiver coupled thereto. This host computer 200 is located within data sending and receiving range of the on-board data acquisition control circuit 160 mounted on the horse 500. Preferably, the radio system operates in a frequency range of about 900 Hz to about 5.8 gigahertz (GHz). However, it is anticipated that other types of radios and or frequency ranges can be used for the same purpose. The subsequent received data is displayed in real time, or approximately real time depending on the sampling rate, such that one can observe the exercise events as they occur (i.e., real-time trending). Some data transformation is performed during the real time observation such that data viewed has some interpretable value or auditory output or the like. For instance, the GPS data proportional to speed is converted to speed. The data is also written as a single file to a hard drive or other memory storage device of the host computer 200. The data may be written as a plurality of separate files in combination or by the particular variable being trended. The host computer 200 also utilizes the LABVIEW software to display the data, i.e., thereby forming a trend display 202 (FIGS. 20A-20E, 21A-21B, and 22A-22D).

The host computer 200 may utilize other software packages commercially available or custom written for the application in order to display the data as a trend, via indicators, bar graphs, data tables or the like. The software may include scaling for variable ranges, units, resolution, alarming, high and low limits or the like. The software may include the ability to overlay multiple variables on the same trend or to display multiple variables on separate trend axes on the same screen (e.g., FIGS. 20A-20E, 21A-21B, and 22A-22D) aligned in time. The stored data file may be in a conventional tabular format, in a database or in a comma-separated-variable (csv) format or the like, which can be imported into a spreadsheet or other data handling software package for manipulation and analysis.

At the conclusion of an exercise event, the enclosure 53, located on the horse 500 is removed, and the data file located in the memory 168 of the on-board data acquisition control circuit 160 is transferred to the host computer 200 or to another backup memory device (i.e., as an historical or data logged file). The data file that resides on the host computer 200 collected via the transceivers 64 can be compared to the data file transferred from the on-board computer/controller 60 to check for missing data that may have resulted from a malfunction of the wireless communication link and/or the computers 60, 200. The redundant saving of data files helps to ensure that an exercise event does not have to be repeated due to data loss.

FIG. 6 is a schematic block diagram depicting a control circuit 260 mounted on a printed circuit PCB in accordance with a second preferred embodiment of the present invention. The control circuit 260 includes a controller U1, a memory U2, an A/D converter U3, a clock X1 and a transmitter or transceiver TX/RX. The controller U1 may be a microprocessor, a microcontroller, an application specific integrated circuit (ASIC) or the like. The controller U1 may include built-in A/D and D/A conversion as well, in addition to or in lieu of the A/D converter U3. The A/D converter U3 has a digital resolution such as 8-24 bit resolution. The control circuit 260 may include a multiplexer U4 for multiplexing a plurality of signals to a single-channel A/D converter U3. Optionally, the A/D converter U3 is a multi-channel A/D chip with built in multiplexing.

The respiratory vibration accelerometer 100, 101 may be hardwired to the control circuit 260 or the control circuit 260 may include an optional wireless receiver 262 for receiving data wirelessly from the optional wireless transmitter 112 of the respiratory vibration accelerometer control circuit 110.

The control circuit 260 may optionally include a built in GPS chipset such that a separate GPS receiver board 165 is not needed. Likewise, the control circuit 260 may optionally include a transmitter or transceiver chip set (e.g., a wireless Ethernet circuit) such that an external transceiver 64 is not needed. The memory U2 may be a flash-RAM chip or a removable flash-RAM card. The control circuit 260 may be implemented on a plurality of printed circuit boards PCBs and/or daughter boards.

FIG. 7 is a schematic block diagram depicting a control circuit 360 mounted on a printed circuit PCB in accordance with a third preferred embodiment of the present invention. The control circuit 360 is similar to the control circuit 260. The control circuit 360 includes a first controller U1, a second controller U10, a first memory U2, a second memory U12, a first A/D converter U3, a second A/D converter U13, a first clock X1, a second clock X2 and a transmitter or transceiver TX/RX. Preferably, the first and second clocks X1, X2 are real time clocks. The controllers U1 and U10 may be a microprocessor, a microcontroller, an application specific integrated circuit (ASIC) or the like. The controllers U1 and U10 may include built-in A/D and D/A conversion as well, in addition to or in lieu of the A/D converters U3 and U13. The A/D converters U3 and U13 have a digital resolution such as 8-24 bit resolution. The control circuit 360 may include a multiplexer U4 for multiplexing a plurality of signals to a single-channel A/D converter U3. Optionally, the A/D converter U3 is a multi-channel A/D chip with built in multiplexing. The first A/D converter U3 may have a first resolution, such as 16-bit resolution, and the second A/D converter U13 may have a second resolution, such as 24-bit resolution. The first controller U1 is coupled to the second controller U10 by a communication bus such as a serial bus, a parallel bus, a USB, an inter-integrated circuit ($I^2C$) bus or the like, in order for the second controller U10 to communicate and/or exchange data with the first controller U1.

The second controller U10, the second memory U12, the second clock X2 and the second A/D converter U13 are dedicated to monitoring the respiratory vibration accelerometer 100, 101. Since the respiratory vibration data has a wide range of frequencies, a higher resolution A/D converter U13 may be desirable along with a dedicated controller U10 to continuously monitor the signal with higher sampling rates than other signals. The respiratory vibration accelerometer 100, 101 may be hardwired to the control circuit 360 or the control circuit 360 may include an optional wireless receiver 362 for receiving data wirelessly from the optional wireless transmitter 112 of the respiratory vibration accelerometer control circuit 110. Alternately, both controllers U1, U10 are linked to the same real time clock X1, X2.

The control circuit 360 may optionally include a built in GPS chipset such that a separate GPS receiver board 165 is not needed. Likewise, the control circuit 360 may optionally include a transmitter or transceiver chip set (e.g., a wireless Ethernet circuit) such that an external transceiver 64 is not needed. The memory U2 and U12 may be a flash-RAM chip or a removable flash-RAM card.

In one configuration, the equine physiological monitoring system 50 includes a portable computer/controller 60, U1, having a memory U2, a lateral-axis angular rate sensor 115, a vertical-axis angular rate sensor 116, a speed sensor 130, 165, an ECG electrode configuration set 128, 129 and a respiratory detection sensor 100, 101. All of the devices are configured to be mounted proximate to a horse 500 so as to move with the horse 500. The lateral-axis angular rate sensor 115 is in communication with the computer/controller 60, U1 and sends the computer/controller 60, U1 detected angular rotation data relative to the lateral-axis. The vertical-axis angular rate sensor 116 is in communication with the computer/controller 60, U1 and sends the computer/controller 60, U1 detected angular rotation data relative to the vertical-axis. The speed sensor 130, 165 is in communication with the computer/controller 60, U1 and sends the computer/controller 60, U1 detected speed data of the horse 500. The ECG electrode configuration set 128, 129 is in communication with the computer/controller 60, U1 and sends the computer/controller 60, U1 detected ECG data. The respiratory detection sensor 100, 101 is in communication with the computer/controller 60, U1 and sends the computer/controller 60, U1 detected respiratory data. The memory 168, U2 at least temporarily stores the detected angular rotation data relative to the lateral-axis, the detected angular rotation data relative to the vertical-axis, the detected speed data, the detected ECG data and the detected respiratory data. Preferably, all of the detected data is synchronized with respect to time as it is acquired and/or stored. Preferably, all of the detected data is synchronized with respect to real time. The synchronized data stored in the memory 168, U2, U12 can be simultaneously viewed in real time or later as an historical trend.

In another configuration, the wireless equine physiological monitoring system 50 includes a respiratory detection sensor 100, 101 and a second sensor 140, each mounted proximate to the horse 500 so as to move with the horse 500 while the horse 500 is exercising over ground (i.e., in a natural environment such as in a field or on a track). In this configuration, the respiratory detection sensor 100, 101 may be a microphone or any other respiratory sensor, and need not be limited to a respiratory vibration accelerometer. The respiratory detection sensor 100, 101 detects and outputs detected respiratory data while the horse 500 is exercising. The second sensor 140 detects and outputs detected second sensor data. The second sensor 140 is at least one of a lateral-axis angular rate sensor 114, 115, 116, a longitudinal-axis angular rate sensor 114, 115, 116, a vertical-axis angular rate sensor 114, 115, 116, an accelerometer 119, 120, 121, a speed sensor 130, 165, an ECG electrode configuration set 128, 129, an EMG sensor configuration set, an EEG sensor configuration set, EOG sensor configuration set, an ZPG sensor configuration set, a pressure sensor, a gas flow sensor, a gas detection sensor, a pH sensor, a temperature sensor, an imaging sensor, an optical sensor and a blood constituent sensor. The trend display 202 or the host computer 200 functioning as a trend display 202 wirelessly receives the detected respiratory data and the detected second sensor data. The trend display 202 or the host computer 200 functioning as a trend display 202 simultaneously displays the detected respiratory data and the detected second sensor data. The displayed data is synchronized with respect to time (i.e., a real-time trend). Preferably, the displayed data is synchronized with respect to real time. Additionally, at least some portions of the respiratory data can be converted and simultaneously outputted as an audible signal in real time while displaying other data that is synchronized with respect to time.

In another configuration, the wireless equine physiological monitoring system, 50 includes a speed sensor 130, 165 and the second sensor 140, each mounted proximate to the horse so as to move with the horse 500. The speed sensor 130, 165 detects and outputs at least one of detected raw data for calculating speed and calculated speed data. The second sensor 140 detects and outputs detected second sensor data. The trend display 202 or the host computer 200 functioning as a trend display 202 wirelessly receives the calculated speed data and the detected second sensor data. The trend display 202 or the host computer 200 functioning as a trend display 202 simultaneously displays the calculated speed data and the detected second sensor data. The simultaneously displayed data is synchronized with respect to time (i.e., a real-time trend). Preferably, all of the displayed data is synchronized with respect to real time.

Alternately, the wireless equine physiological monitoring system 50 includes a speed sensor (not shown in detail) that monitors the speed of the horse 500 remotely from the horse 500 and transmits the remotely acquired speed data to the host computer 200 and/or to the on-board control circuit 160, 260, 360. The remote speed monitoring may be performed using one or more of.

Doppler radar, transponder-based Doppler speed determination, pseudolite-based Doppler speed determination, optical ground pattern recognition, continuous or pulsed sonar, cellular telephone triangulation, cellular telephone timelapse, radio-direction finder with distance measuring equipment (DME), very high frequency (VHF) omni-directional ranging with DME, Rayleigh fading, Doppler multi-path spreading, pseudolite triangulation and ranging, anemometer, light direction and ranging (LIDAR), optical tracking, optical DME, RF ranging and triangulation, stopwatch/chronograph or the like. Preferably, the remotely acquired speed data is also synchronized with respect to time and the various clocks X1 are able to be synchronized with respect to each other. Preferably, all of the data is synchronized with respect to real time.

In another configuration, the wireless equine physiological monitoring system 50 includes a single-axis angular rate sensor 114, 115, 116 mounted proximate to a horse 500 so as to move with the horse 500. The single-axis angular rate sensor 114, 115, 116 detects and outputs angular rotation data relative to the single-axis. The trend display 202 or the host computer 200 functioning as a trend display 202 wirelessly receives the detected angular rotation data relative to the single-axis. The trend display 202 or the host computer 200 functioning as a trend display 202 displays the detected angular rotation data relative to the single-axis with respect to time as the detected angular rotation data relative to the single-axis is received (i.e., a real-time trend).

In another configuration, the respiratory vibration accelerometer 100, 101 is attached to one of hair, skin, bone, ligament, cartilage, and other tissue of a horse 500, so that the respiratory vibration accelerometer 100, 101 detects respiratory structural vibration data. Either a transceiver (not shown) sends the respiratory structural vibration data to the computer/controller 60 or the transceiver (not shown) sends the data to the host computer 200. Either the on-board computer/controller 60 or the transceiver 64 converts the respiratory structural vibration data to a corresponding signal and wirelessly transmits the corresponding signal to a receiving device. The wirelessly transmitted data is received at an audio generating device such as a host computer 200 having a speaker 201 or a simple hand-held radio (e.g., a walkie-talkie) having a speaker (not shown). The detected respiratory structural vibration data is stored at the on-board data acquisition control circuit 160 and/or the host computer 200 while the audio generating device simultaneously emits audible sound, in real time, based on the corresponding signal. This allows an observer to "listen" to portions of the respiratory data (i.e., within the audible range) while observing other trends or observing the exercising horse or the like, while still being able to store the respiratory data for later retrieval and historical analysis.

It is contemplated that the on-board data acquisition control circuit 160 can be a conventional MP3 player/recorder that receives a signal input, performs analog to digital conversion (A/D) and stores the received signal in a compressed data file. It is also contemplated that the on-board data acquisition control circuit 160 can be a commercially available data logger such as a DI-710 Data Logger commercially available from Dataq Instruments, Inc., Akron, Ohio.

FIGS. 20A-20E show a condensed five (5) second display of the output from multiple sensors 128, 129, 115, 116, 100, 101, 130, 165 while a horse 500 is trotting. Any combination of graphs or trends may be simultaneously displayed on the trend display 202 without departing from the invention. Preferably the trends are all time synchronized so that particular events can be detected easily. Preferably, the trends are all time synchronized in real time. However, the trends can also be displayed singly and/or only historically.

Figure 20D:
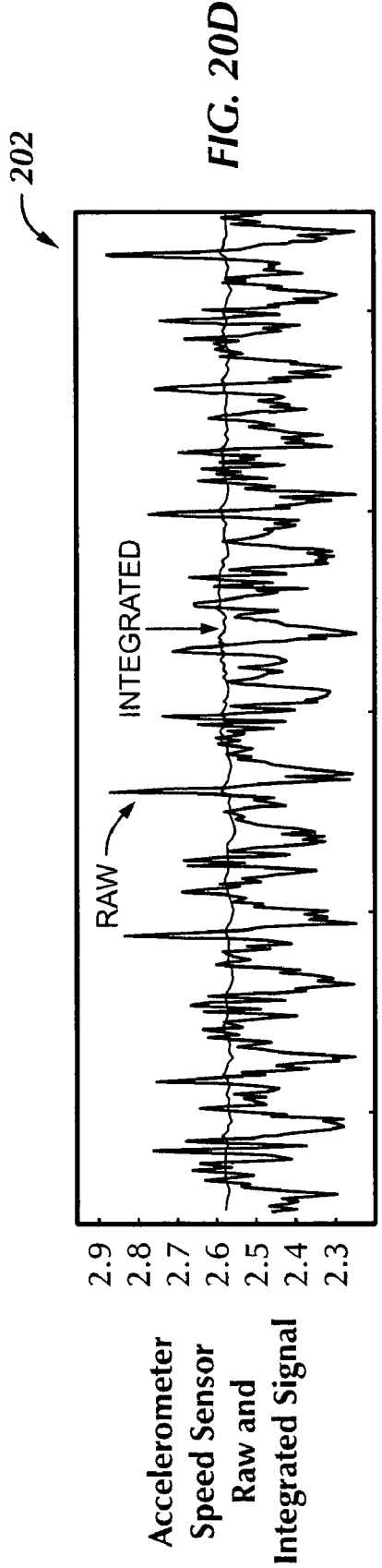
Figure 20E:
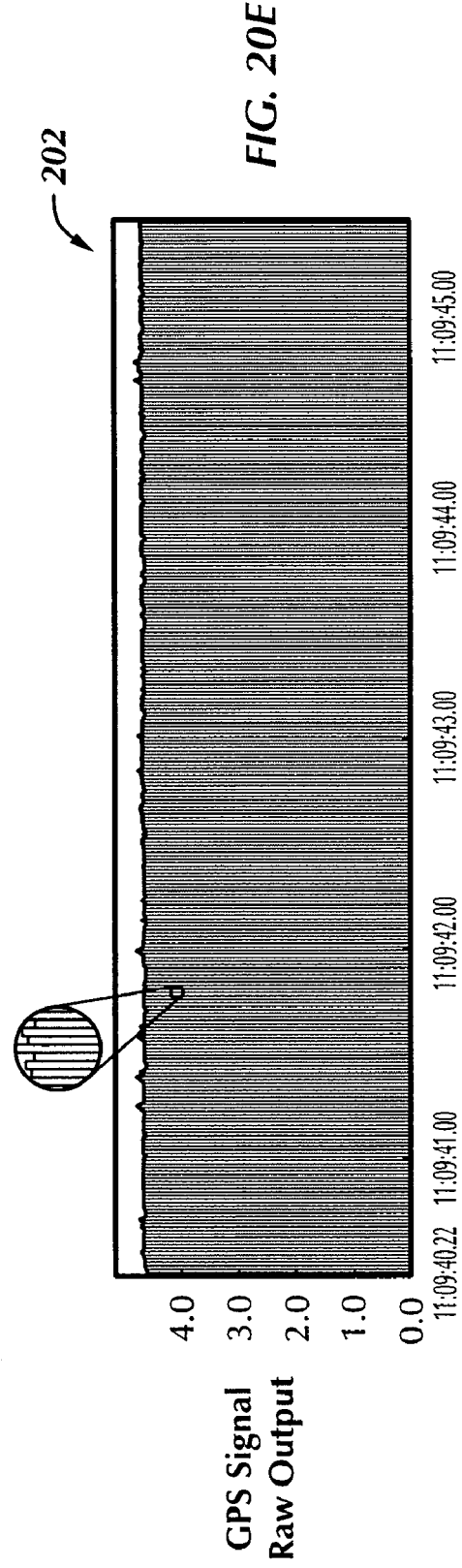

FIG. 20A shows ECG data with a normal rhythm (no arrhythmias) and a calculated heart rate of 60 beats per minute (BPM) being displayed on the trend display 202. FIG. 20B shows data from the lateral-axis and vertical axis angular rate sensors 115, 116 which is also displayed on the trend display 202. This trend display gives an indication that respiration and locomotion are out of phase as well as how the horse 500 is modulating the stiffness of its body and limbs. Further, data from the lateral axis sensor 115 demonstrates that the horse 500 is taking seven (7) strides per five (5) seconds (i.e., 1.4 strides per second), and data from the vertical axis angular rate sensor 116 confirms the stride rate and also demonstrates which diagonal the horse 500 is exhibiting. FIG. 20C shows data from the respiratory vibration accelerometer 100, 101 being displayed on the trend display 202. These data represent accelerations of the respiratory structural changes that are occurring during exercise and the potential influences of the locomotor and cardiovascular systems on these structures. In addition, the respiratory structural vibrations can be used to ascertain the overall as well as the inspiratory and expiratory respiratory segments and any irregularities thereof. FIGS. 20D-20E shows data from either the speed accelerometer 130 or GPS receiver board 165, raw and/or integrated data, being displayed on the trend display 202. The voltage output shown in FIG. 20D is converted to acceleration (feet/second 2) using the manufacturer's specifications and then calculating the first integral which yields speed in feet per second (ft/sec) indicated by the line labeled "integrated" on the trend of FIG. 20D. It can be appreciated that one can ascertain the speed of the horse 500. These speed measurements can be used to evaluate cardiac rhythm and rate at various speeds as well as at what speeds respiratory locomotor events are occurring. In addition, these speed measurements are used to calculate various respiratory locomotor variables. A basic example is the calculation of stride length by the formula:

Stride length=speed/stride frequency

The raw GPS signal output shown on the bottom trend of FIG. 20E can be used for the same purpose as the speed accelerometer data. In this case the signal is first converted to speed by the formula:

45 Hz=1 MPH thus, yielding a speed measurement every 0.1 seconds based on the update rate of GPS receiver 165 of at least 10 times per second. It is anticipated that other models of GPS receiver 165 and/or manufacturers will have different methods of outputting speed measurements.

It is desirable to identify at what speed a particular physiological event occurs. For example, it is of interest to know if an arrhythmia occurs when the horse 500 exceeds 25.5 MPH or that the horse 500 has a respiratory locomotor phase shift when the horse 500 exceeds 30.2 MPH or the like. This is especially true if the identified physiological event is relatively repeatable for a given horse 500.

Preferably, the data is all synchronized with respect to time to permit a user to more easily identify interactions between the monitored physiological data. Preferably, the data is synchronized with respect to time as the data is acquired and stored or acquired and transmitted. Preferably, all of the data is synchronized with respect to real time.

Figure 21A:
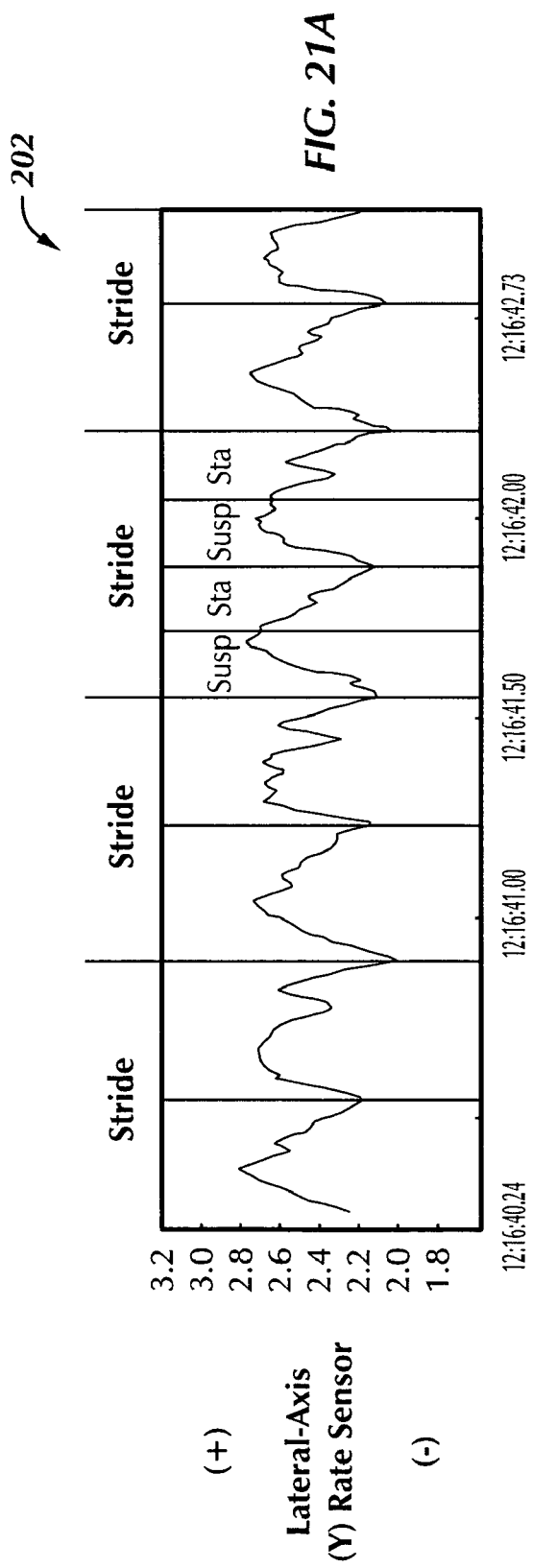
FIGS. 21A-21B are screen shots of a trend display having an angular-rate motion sensor trends synchronized in time in accordance with the preferred embodiments of the present invention.
Figure 21B:
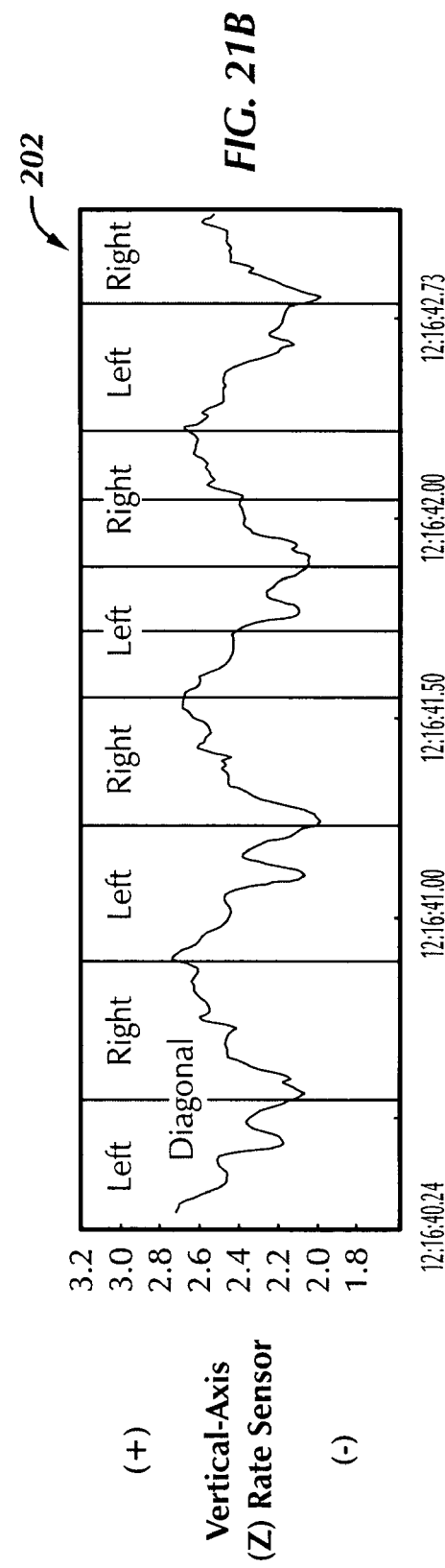

FIGS. 21A-21B show a 2.5 second time period to illustrate use of the angular rate sensors 114, 115, 116 to determine stride frequency and basic components of the trotting stride of a horse 500. FIG. 21A shows data from the lateral-axis angular rate sensor 115 which clearly demonstrates four (4) strides per 2.5 seconds, thus a stride frequency of 1.6 strides per second. FIG. 21B shows data from the vertical-axis angular rate sensor 116 which confirms the stride frequency and also identifies which diagonal the horse 500 is exhibiting during each half of the stride. Rotation of the sensor in the negative direction signifies that the left front leg and right rear leg are moving forward. Thus, by convention, the horse 500 is said to be exhibiting the "left diagonal" likewise as the sensor rotates in the positive direction the right front leg and the left rear leg are moving forward thus by convention the horse 500 would be exhibiting the "right diagonal". In addition, the suspension and stance phases that occur during each diagonal of the trotting stride are noted. In addition, this horse 500 is exhibiting a locomotion disorder.

FIGS. 22A-22D show a 2.5 second display of a horse 500 galloping. FIG. 22A shows data from the lateral-axis angular rate sensor 114, 115, 116 demonstrating that the stride frequency is 5 strides per 2.5 seconds, or 2 strides per second. FIG. 22B shows data from the vertical-axis angular rate sensor 116 that confirms the gallop frequency of 2 strides per second and also identifies by its phase shift relative to the lateral-axis angular rate sensor 114, 115, 116 waveform that the horse 500 is on its left lead. If the horse 500 were on its right lead then the major stride components exhibited by the vertical-axis angular rate sensor 114, 115, 116 would be shifted to the left. The respiratory accelerometer 100, 101 sensor output charted in FIG. 22C shows that the overall respiratory cycle is synchronized in a 1:1 ratio with the overall gallop cycle and that the inspiratory and expiratory portions of respiration occur during specific phases of the gallop stride cycle, i.e., that inspiration mainly occurs during the suspension phase of the stride and that expiration mainly occurs during the stance phase of the stride. FIG. 22D shows an ECG signal of 5 beats per 2.5 seconds yields a heart rate of 120 BPM. Because the trace is an ECG signal and not just a heart rate monitor, it is possible to discern that there are no arrhythmias present in this trace.

The data can be displayed with respect to the time domain, the frequency domain and their amplitudes and/or a combination of the time domain and the frequency domain and amplitudes. Converting sensor data between the time domain and the frequency domain and vice-versa is within the scope of the present invention.

The above examples illustrate how one can obtain simultaneous information regarding the respiratory, locomotive, and cardiovascular systems of the exercising horse 500 in order to assist in observing their interactions during exercise events of the horse 500. Those skilled in the art can appreciate that with further analysis, one can study the interactions of the physiological and biometric systems of the exercising horse 500. Further, this method allows those skilled in the art, such as an equine veterinarian, to identify and analyze differences, irregularities and abnormalities within and between each of the systems of a single horse 500 or multiple horses 500.

The equine physiological monitoring system 50 can be used in the study of varying ground and climatic conditions, genotypes, phenotypes, feeding and training strategies, influences of riders 540, drivers, or unencumbered by either, riding, driving equipment and training aids, pharmacological agents, medical and developmental histories, shoeing, metabolic, physiologic and psychological states, and intra and inter species communications and vocalizations.

While the present invention has been described with respect to horses 500, embodiments of the present invention are also equally applicable with other animals such as camels, dogs, elephants or the like.

From the foregoing, it can be seen that the present invention comprises a portable wireless equine physiological monitoring system and a method for using the equine physiological monitoring system. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method of monitoring physiological data of an exercising horse comprising:
   (a) mounting a sensing surface of an accelerometer directly to one of hair and skin of a horse, the accelerometer detecting respiratory structural vibration data;
   (b) exercising the horse;
   (c) converting the respiratory structural vibration data to a corresponding signal and wirelessly transmitting the corresponding signal;
   (d) receiving the wirelessly transmitted corresponding signal at an audio generating device, the audio generating device emitting audible sound in generally real time based on the corresponding signal; and
   (e) storing, at least temporarily in a memory mounted proximate to the horse, the detected respiratory structural vibration data, wherein at least one of the accelerometer and the memory is configured for wireless communication of the detected respiratory structural vibration data.

2. The method according to claim 1, further comprising:
   (f) displaying, on one of a trend display and a computer, the respiratory structural vibration data.

3. The method according to claim 1, further comprising:
   (f) playing back the respiratory structural vibration data stored in the memory as one of a graphical trend and an audible sound.

* * * * *